United States Patent [19]

Fareed et al.

[11] Patent Number: 5,242,823

[45] Date of Patent: Sep. 7, 1993

[54] CLONING OF THE 38KD MYCOPLASMA HYORHINIS REGRESSION-ASSOCIATED ANTIGEN

[75] Inventors: George C. Fareed, Los Angeles; Arup Sen, Van Nuys; Pradip Ghosh-Dastidar; Lee Jar-How, both of Los Angeles, all of Calif.

[73] Assignee: International Genetic Engineering, Inc., Santa Monica, Calif.

[21] Appl. No.: 956,546

[22] Filed: Oct. 2, 1992

Related U.S. Application Data

[63] Continuation of Ser. No. 474,730, Mar. 16, 1990, abandoned, which is a continuation-in-part of Ser. No. 131,815, Dec. 11, 1987, abandoned, and a continuation-in-part of Ser. No. 97,910, Sep. 16, 1987, abandoned, which is a continuation-in-part of Ser. No. 138,923, Jan. 4, 1988, abandoned, which is a continuation-in-part of Ser. No. 837,494, Mar. 7, 1986, Pat. No. 4,748,112.

[51] Int. Cl.$^5$ .............. C12P 21/02; C07H 15/12; C07H 3/00; C12N 1/20

[52] U.S. Cl. .............. 435/252.3; 435/69.1; 435/69.3; 435/252.33; 435/320.1; 530/350; 530/403; 530/806; 530/825; 536/23.7; 424/88

[58] Field of Search .............. 530/350, 403, 806, 825; 536/27; 435/691, 693

[56] References Cited

U.S. PATENT DOCUMENTS

| | | | |
|---|---|---|---|
| 3,585,179 | 6/1971 | Samejima et al. | 260/112 |
| 4,100,149 | 7/1978 | Meiller et al. | 260/112 R |
| 4,331,647 | 5/1982 | Goldenberg | 421/1 |
| 4,340,535 | 7/1982 | Voisin et al. | 260/112 B |
| 4,348,376 | 9/1982 | Goldenberg | 424/1 |
| 4,358,535 | 11/1982 | Falkow et al. | 435/5 |
| 4,383,985 | 5/1983 | Bartorelli et al. | 424/1 |
| 4,415,732 | 11/1983 | Caruthers | 536/27 |
| 4,444,744 | 4/1984 | Goldenberg | 424/1.1 |
| 4,452,290 | 6/1984 | Haagensen, Jr. | 436/545 |
| 4,472,509 | 9/1984 | Gansow et al. | 436/548 |
| 4,486,539 | 12/1984 | Ranki | 436/504 |
| 4,517,303 | 5/1985 | Freytag et al. | 436/501 |
| 4,543,211 | 9/1985 | Kato et al. | 260/112 B |
| 4,559,311 | 12/1985 | Stenman et al. | 436/542 |
| 4,562,160 | 12/1985 | Real et al. | 436/539 |
| 4,568,488 | 2/1986 | Lee-Huang . | |
| 4,584,268 | 4/1986 | Ceriani et al. | 435/7 |
| 4,705,677 | 11/1987 | Makari | 424/1.1 |
| 4,748,112 | 5/1988 | Fareed et al. | 435/7 |

FOREIGN PATENT DOCUMENTS

| | | |
|---|---|---|
| 027816 | of 0000 | European Pat. Off. . |
| 0062286 | of 0000 | European Pat. Off. . |
| 0237252 | of 0000 | European Pat. Off. . |
| WO87/05301 | of 0000 | PCT Int'l Appl. . |

OTHER PUBLICATIONS

Wise, K. S., "Antigen Expression from Cloned Genes of *Mycoplasma hyorhinis:* an approach to Mycoplasma Genomic Analysis", *Chemical Abstract* 102:183595q, 1985.

(List continued on next page.)

*Primary Examiner*—Christine M. Nucker
*Assistant Examiner*—Michael Tuscan
*Attorney, Agent, or Firm*—Marshall, O'Toole, Gerstein, Murray & Borun

[57] ABSTRACT

Regression associated antigens (RAAs) are identified in material from neoplastic cells by their immunological reactivity with regression associated antibodies from the serum of patients diagnosed as undergoing regression of a tumor. Regression associated antibodies (RAAbs) are identified by their absence during progression of a neoplastic disease state and by their presence in a diagnosed state of regression. RAAs have been purified and used to monitor the condition of cancer patients. Production of RAAbs and treatments employing those antibodies are described. It is herein disclosed that RAAs are expressed by *M. hyorhinis* and are also expressed by expression of provided nucleotide sequences in recombinant host cells, particularly nucleotide sequence for 38 kd and 43 kd RAAs as expressed in *E. coli*. RAAs and nucleic acids encoding RAAs (or portions thereof) and RAAbs may be used in diagnostic assays and immunotherapy. RAAbs and fragments portion thereof may be used in passive immunization therapy and radioisotope or magnetic resonance scanning.

```
GCGTTATTAT AAAAAATAAA AATTTAAAAA GTAATGTAAA AATTTAATTT ACATTACTTT TTTTGTATAA TTATTTCAAC

AGGGGTGCTG TAAAAGGTTG AGAAATACTC TATAAGTTGA TCTAGATAAT GCTAGCGTAA CGAGTTGTTT TTTATTTTCA
                                                                 •  •        •
                                                         LEU LEU LYS LYS PHE LYS ASN PHE
AATTTTTAAA GCTATCTCTG TCACAAAAAT TAATTAACGG AGGTAGCTTT TTTG CTC AAA AAA TTT AAA AAT TTT

ILE LEU PHE SER SER ILE PHE SER PRO ILE ALA PHE ALA ILE SER CYS SER ASN THR GLY VAL VAL
ATT CTA TTT TCA TCT ATA TTT TCG CCA ATA GCA TTT GCT ATA TCA TGT TCT(AAT ACA GGA GTA GTC
  •   •   •                                 •  •                                    •
LYS GLN GLU ASP  VAL SER VAL SER GLN GLY GLN TRP ASP LYS SER ILE THR PHE GLY VAL SER GLU
AAG CAA GAG GA|T GTA TCA GTT AGT CAA GGT CAA TGA GAT AAA AGT ATA ACA TTT GGT GTT TCA GAA
                    •  •      •  •          •  •                   •
ALA TRP LEU ASN LYS LYS LYS GLY GLY LYS GLU VAL ASN LYS GLU VAL ILE ASN THR PHE LEU GLU
GCT TGG TTA AAC AAG AAA AAA GGA GGT AAA GAA GTT AAC AAA GAA GTT ATT AAT ACA TTT TTA GAA
HindIII                                          HpaI
```

OTHER PUBLICATIONS

Taylor, M. A. "Cloned Genomic DNA Sequences from *Mycoplasma hyorhinis* encoding antigens expressed in *Escherichia coli*" Proc. Natl. Acad. Sci. 80:4154–4158, 1983.
Bast et al., Proceedings of the UCLA Symposium on Monoclonal Antibodies and Cancer Therapy, Reisfeld et al. eds., A. R. Liss, Inc., New York, pp. 37–51 (1985).
Ben-Aissa et al., Br. J. Cancer, 52, 65–72 (1985).
Beutler et al., Science, 229, 869–871 (1985).
Cepko et al., Cell, 37, 1053–1062 (1984).
Bitter et al., Gene, 32, 263–274 (1984).
Blakely et al., BioEssays, 4(6), 292–297.
Bornkamm et al., Curr. Top. Microbiol. Immul., 104, 288–298 (1983).
Brahic et al., Proc. Nat'l. Acad. Sci. (USA), 75, 6125–6129 (1978).
Brown et al., J. Immunology, 127(2), 539–547 (1981).
Martin, et al., J. Immunology, 131.
Bubbers et al., Bull. Cancer, 68, 332–337 (1981).
Butler et al., Infect. Immun., 42, 1136–1143 (1983).
Capony et al., Biochem. Biophys. Res. Commun., 108, 8–15 (1982).
Casadaban et al., J. Mol. Biol., 138, 179–207 (1980).
Towbin et al., Proc. Nat'l. Acad. Sci. (USA), 76, 4350–4354 (1979).
Tsu et al., Selected Methods in Cellular Immunol., Mishell et al. eds., Freeman Publishing Co., San Francisco, 3737–397 (1980).
Van Diggelen et al., Cancer Res., 37, 2680–2687 (1977).
Van Diggelen et al., Exp. Cell Res., 106, 191–202 (1977).
Van Regenmortel, TIBS, 11, 36–39 (1986).
Vandekercknove et al., Eur. J. Biochem., 152, 9–19 (1985).
Yuen, et al., Applied Bio-Systems User Bulletin No. 25 (1986).
Vennegoon et al., Exp. Cell Res., 137, 89–94 (1982).
Viera et al., Gene, 19, 259≠268 (1982).
Wallack et al., Surgery, 96, 791–800 (1984).
Weinstein et al., Proceedings of the UCLA Symposium on Monoclonal Antibodies and Cancer Therapy, A. R. Liss, Inc., New York, Reisfeld et al. eds., pp. 473–488 (1985).
Weir ed., Handbook of Experimental Immunology, Blackwell Scientific Publications, vol. 3, A3.1–A4.10 (1978).
Weisenburger et al., J. Biol. Resp. Mod., 1, 57–66 (1982).
Wise et al., Infect. Immun., 48(2), 587–591 (1985).
Rodwell et al., Biotechnology, 3, 889–894 (1985).
Rosenberg et al., New Engl. J. Med., 313, 1485–1492 (1985).
Sanger et al., Proc. Nat'l. Acad. Sci. (USA), 74, 5463 (1977).
Schlom et al., Cancer, 54, 2777–2794 (1984).
Sen et al., Proc. Nat'l. Acad. Sci. (USA), 80, 1246–1250 (1983).
Sheehan et al., Theory and Practice of Histotechnology, eds., C. V. Masby Co., 310–326 (1980).
Southern et al., J. Mol. Biol., 98, 503 (1975).
Springer, Science, 224, 1198–1206 (1984).
Srivastava et al., Proc. Nat∝l. Acad. Sci. (USA), 83, 3407–3411 (1986).
Steinemann et al., Proc. Nat'l. Acad. Sci. (USA), 81, 3747–3750 (1984).
Stevenson et al., Bioscience Reports, 5, 991–998 (1985).
Thomas, Proc. Nat'l. Acad. Sci. (USA), 77, 5201–5205 (1980).
Maniatis et al., Molecular Cloning, Cold Spring Harbor Laboratory, Cold Spring Harbor, New York (1982).
Marglin et al., Ann Rev. Biochem., 39, 841–866 (1970).
Masson et al., Nucleic Acids Res., 14(14), 5693–5711 (1986).
Melton et al., Nucleic Acids Res., 12, 7034–7055 (1984).
Sell, Proceedings of the UCLA Symposium on Monoclonal Antibodies and Cancer Therapy, A. R. Liss, Inc., New York, Reisfeld et al. eds., pp. 3–21 (1985).
Metzger et al., Proceedings of the UCLA Symposium on Monoclonal Antibodies and Cancer Therapy, A. R. Liss, Inc., New York, Reisfeld et al eds., pp. 63–74 (1985).
Mitchell, Proceedings of the UCLA Symposium on Monoclonal Antibodies and Cancer Therapy, A. R. Liss, Inc., New York, Reisfeld et al. eds., pp. 495–503 (1985).
Moy et al., J. Surg. Oncol., 29, 112–117 (1985).
Mule et al., J. Immunol., 135, 646–652 (1985).
Niman et al., Proc. Nat'l. Acad. Sci. (USA), 80, 4949–4953 (1983).
Novotny et al., Proc. Nat'l. Acad. Sci. (USA), 83, 226–230 (1986).
Parish et al., J. Cell. Sci., Suppl. 8, 181–197 (1987).
Pierce et al., Ann. Rev. Biochem. 50, 465–495 (1981).

Rigby et al., Mol. Biol., 113, 237–251 (1977).
Kan-Mitchell, Proceedings of the UCLA Symposium on Monoclonal Antibodies and Cancer Therapy, A. R. Liss, Inc., New York, Reisfeld et al. eds., pp. 523–536 (1985).
Kemeny et al., J. Immunol. Methods, 87, 45–50 (1986).
Key et al., Adv. Immun. Cancer Ther., 1, 195–219 (1985).
Key et al., J. Biol. Response Mod., 3, 359–365 (1984).
Kohler et al., Nature, 256, 495–496 (1975).
Kramer et al., Nucleic Acids Res., 12, 9441–9456 (1984).
Lachman et al., Br. J. Cancer, 51, 415–417 (1985).
Laemmli, Nature, 227, 680–685 (1970).
Laucius et al., Cancer, 40, 2091–2093 (1977).
Lauterbur, P. C., in Accomplishments in Cancer Research 1985, Fortner et al. eds., J. B. Lippencott Co., pp. 47–57 (1986).
Law et al., Cancer Research, 47, 5841–5845 (1987).
Leary et al., Proc. Nat'l. Acad. Sci., 80, 4045–4049 (1983).
Lerner, Nature, 299, 592–596 (1982).
Lowder et al., Western J. Med., 143, 810–818 (1985).
Hellstrom et al., Proceedings of the UCLA Symposium on Monoclonal Antibodies and Cancer Therapy, A. R. Liss, Inc., New York, Reisfeld et al. eds., pp. 149–164 (1985).
Hellstrom et al., Cancer Res., 46, 3917–3923 (1986).
Herrmann et al., J. Cell Sci., 73, 87–103 (1985).
Hollinshead et al., Cancer, 60(6), 1249–1262 (1987).
Hood et al., Immunology, Benjamin/Cummings Publishing Co., pp. 189–196, 202–208, 487–534 (1984).
Hsu et al., Proceedings of the UCLA Symposium on Monoclonal Antibodies and Cancer Therapy, A. R. Liss, Inc., New York, Reisfeld et al. eds., pp. 53–61 (1985).
Hoover et al., Cancer Res., 44, 1671–1676 (1984).
Jack et al., TIBTECH, 5, 91–95 (1987).
Jessup et al., Arch. Surg., 122, 1435–1439 (1987).
Johnston et al., Gene, 34, 137–145 (1985).
Juillard et al., Cancer, 41, 2215–2225 (1978).
Juillard et al., Bull. Cancer, 66, 217–228 (1979).
Kafatos et al., Nuc. Acids Res., 7, 1541–1552 (1979).
Du Bois et al., J. Immunol. Methods, 63, 7–24 (1983).
Dudler et al., EMBOJ, 7(12), 3963–3970 (1988).
Dunn et al., Cell, 12, 23–36 (1977).
Eichmann et al., CRC Crit. Rev. Immunol., 7, 193–227 (1987).
Fareed et al., Chem. Abst. 108 No. 13, Abst 110436c, Mar. 28, 1988.
Feinberg et al., Anal. Biochem., 132, 6–13 (1983).
Feit et al., Cancer Res., 44, 5752–5756 (1984).
Fernsten et al., Cancer Res., 46, 2970–2977 (1986).
Fernsten et al., Infect. Immunity, 55(7), 1680–1685 (1987).
Giard et al., J. Nat. Cancer Inst., 51, 1417–1423 (1973).
Glassy et al., Proceedings of the UCLA Symposium on Monoclonal Antibodies and Cancer Therapy, A. R. Liss, Inc., New York, Reisfeld et al. eds., pp. 97–109 (1985).
Gorman et al., Mol. Cell. Biol., 2, 1044–1051 (1982).
Gussack et al., Cancer, 62, 283–290 (1988).
Hand et al., Proceedings of the UCLA Symposium on Monoclonal Antibodies & Cancer Therapy, A. R. Liss, Inc., New York, Reisfeld et al., eds., pp. 23–36 (1985).
Young et al., Proc. Nat'l. Acad. Sci. (USA), 80, 1194–1198 (1983).
Young et al., Proc. Nat'l. Acad. Sci. (USA), 85, 4267–4270 (1988).

FIG. 1/1

GCGTTATTAT AAAAAATAAA AATTTAAAAA GTAATGTAAA AATTTAATTT ACATTACTTT TTTTGTATAA TTATTCAAC

AGGGGTGCTG TAAAAGGTTG AGAAATACTC TATAAGTTGA TCTAGATAAT GCTAGCGTAA CGAGTTGTTT TTTATTTCA

```
                                                              LEU LEU LYS LYS PHE LYS ASN PHE
AATTTTTAAA GCTATCTCTG TCACAAAAAT TAATTAACGG AGGTAGCTTT TTTG CTC AAA AAA TTT AAA AAT TTT
                                                 *              *
ILE LEU PHE SER SER ILE PHE SER PRO ILE ALA PHE ALA ILE SER CYS SER ASN THR GLY VAL VAL
ATT CTA TTT TCA TCT ATA TTT TCG CCA ATA GCA TTT GCT ATA TCA TGT TCT AAT ACA GGA GTA GTC
     *       *                   *                      *
LYS GLN GLU ASP VAL SER VAL SER GLN GLY GLN TRP ASP LYS SER ILE THR PHE GLY VAL SER GLU
AAG CAA GAG GAT GTA TCA GTT AGT CAA GGT CAA TGA GAT AAA AGT ATA ACA TTT GGT GTT TCA GAA
         *                                        *              *                      *
ALA TRP LEU ASN LYS LYS GLY GLY LYS GLU VAL ASN LYS GLU VAL ILE ASN THR PHE LEU GLU
GCT TGG TTA AAC AAG AAA AAA GGA GGT AAA GAA GTT AAC AAA GAA GTT ATT AAT ACA TTT TTA GAA
    HindIII                                      HpaI
```

FIG. 1/2

```
ASN PHE LYS GLU PHE ASN LYS LEU LYS ASN ALA ASN ASP LYS THR LYS ASN PHE ASP VAL
AAT TTC AAA GAA TTT AAT AAA CTC AAA AAT GCA AAT GAT AAA ACC AAA AAC TTC GAT GAC GTT

ASP PHE LYS VAL THR PRO ILE GLN ASP PHE THR VAL LEU LEU ASP LYS ASN LEU SER THR ASP ASN PRO
GAT TTT AAA GTA ACT CCA ATT CAA GAC TTT ACT GTG TTG TTA GAT AAA AAC TTA TCT ACT GAC AAT CCT

GLU LEU ASP PHE GLY ILE ASN ALA SER GLY LYS LEU VAL GLU PHE LEU ASN ASN PRO GLY ILE
GAA TTA GAT TTT GGA ATT AAT GCT TCA GGA AAA TTG GTA GAA TTT CTA AAA AAT AAT CCT GGT ATA

ILE THR PRO ALA LEU GLU THR THR ASN SER PHE VAL PHE ASP LYS GLU LYS PHE TYR
ATA ACT CCA GCA TTA GAA ACA ACA ACT AAT TCT TTT GTA TTT GAC AAA GAA AAA TTT TAT

VAL ASP GLY THR ASP SER ASP PRO LEU VAL LYS ILE ALA LYS GLU ILE ASN LYS ILE PHE VAL GLU
GTT GAT GGT ACA GAT TCA GAT CCA CTT GTA AAA ATT GCT AAA GAA ATT AAT AAA ATT TTT GTT GAA
```

FIG. 1/3

```
THR PRO TYR ALA SER(TRP)THR ASP GLU ASN HIS LYS(TRP)ASN GLY ASN VAL TYR GLN SER VAL TYR
ACT CCA TAT GCA AGT TGA ACT GAT GAA AAT CAT AAG TGA AAT GGT AAT GTT TAT CAA AGT GTT TAC
                                                                                    AluI
         *                     *                     *                     *

ASP PRO THR VAL GLN ALA ASN PHE TYR ARG GLY MET ILE(TRP)ILE LYS GLY ASN ASP GLU THR LEU
GAT CCA ACT GTT CAA GCT AAT TTT TAT AGA GGA ATG ATT TGA ATA AAA GGT AAT GAT GAA ACT CTA
         *                     *                     *                     *

ALA LYS ILE LYS LYS ALA(TRP)ASN ASP LYS ASP(TRP)ASN THR PHE ARG ASN PHE GLY ILE LEU HIS
GCT AAA ATT AAA AAA GCT TGA AAT GAT AAA GAT TGA AAT ACA TTT AGA AAT TTT GGA ATT TTA CAC
         *                     *                     *                     *
              AluI-HindIII GLY LYS ASP ASN SER SER LYS PHE LYS LEU GLU GLU THR ILE LEU LYS ASN HIS PHE GLN ASN
GGT AAA GAT AAT TCT TCT AAA TTC AAG TTA GAA GAA ACT ATA TTA AAA AAC CAC TTT CAA AAT
              MboII/MboII
    *                          *
```

FIG. 1/4

```
      *
LYS PHE THR THR LEU ASN GLU ASP ARG SER ALA HIS PRO ASN ALA TYR LYS GLN LYS SER ALA ASP
AAA TTT ACA ACA CTA AAT GAA GAC AGA AGC GCA CAT CCA AAC GCA TAT AAA CAA AAA TCT GCA GAT
        ___ ___         ___         ___                 ___                     ___
                     MboII                 HhaI                                  PstI

*                                *                 *
THR LEU GLY THR LEU ASP ASP PHE HIS ILE ALA PHE SER GLU GLU GLY SER PHE ALA(TRP)THR HIS
ACA TTG GGA ACT TTA GAT GAT TTC CAT ATT GCT TTT TCA GAA GAA GGT TCT TTT GCT TGA ACA CAT
    ___     ___ ___         ___ ___ ___ ___     ___                 ___ ___     ___ ___
                                                      MboII

*
ASN LYS SER ALA THR LYS PRO PHE GLU THR LYS ALA ASN GLU LYS MET GLU ALA LEU ILE VAL THR
AAC AAA TCA GCA ACA AAA CCT TTT GAA ACT AAA GCA AAT GAA AAG ATG GAA GCA CTT ATA GTA ACT
        ___ ___ ___         ___     ___ ___     ___             ___     ___ ___ ___ ___

ASN PRO ILE PRO TYR ASP VAL GLY VAL PHE ARG LYS SER VAL ASN GLN LEU GLU GLN ASN LEU ILE
AAT CCA ATT CCG TAT GAT GTT GGA GTG TTT AGA AAA AGT GTT AAC CAA TTA GAA CAA AAT TTA ATT
        ___     ___     ___     ___ ___         ___ ___             ___         ___ ___
                                                    HpaI
```

FIG. 1/5

| VAL | GLN | THR | PHE | ILE | ASN | LEU | ALA | LYS | ASN | LYS | GLN | ASP | THR | TYR | GLY | PRO | LEU | LEU | GLY | TYR | ASN |
|---|---|---|---|---|---|---|---|---|---|---|---|---|---|---|---|---|---|---|---|---|---|
| GTT | CAA | ACA | TTC | ATT | AAT | TTA | GCT | AAA | AAT | AAA | CAA | GAT | ACA | TAT | GGT | CCA | CTT | TTA | GGG | TAT | AAT |

AluI

| GLY | TYR | LYS | LYS | ILE | ASP | ASN | PHE | GLN | LYS | GLU | ILE | VAL | GLU | VAL | TYR | GLU | LYS | ALA | ILE | LYS | END |
|---|---|---|---|---|---|---|---|---|---|---|---|---|---|---|---|---|---|---|---|---|---|
| GGT | TAT | AAA | AAA | ATT | GAC | AAT | TTC | CAA | AAA | GAG | ATT | GTA | GAA | GTT | TAT | GAA | AAA | GCC | ATT | AAA | TAA |

ATT AGA AAT AAA AAA TTT AAC ATT TAA AAA TGA TTA CAT AAT TTT AAA GAA CCT AAA

CTT AGA TAT AAA TTC TGA TAA AGT TTT GTT TTT ATT AGG TTC ATC CAG GCC

HaeIII

FIG. 3/1

CTACAGTTATA GGTAATGGAA GTGGAATTTT CGAAAGTATT AAAACTTATC AAAATATTTT CTATTTATTA CCATATTTAG
                                             TaqI                                SspI

TAACATTAAT AATATTAATA TTTACATCAA AAAATACAAT TGCTCCAAAA GCAGTCGGTC TTCCTTATGA CAAATCATTG
           SspI   SspI

AGGTAGAAGA TCAAAAACTT TATATTTTT TTGTTTTTAT GGTATATTAT GTTTTTAAAT TGTACATTTA ATTATTAAGT
                                                                     RsaI

Met Asn Phe Lys Lys Ser Leu Leu Phe Leu Thr Gly
                                                    ATG AAT TTT AAA AAA TCA TTA TTA TTT TTA ACA GGA
GAGGTGAATT T                                                            45                      60
                                                                 MATURE N-TERMINUS
Thr Ile Ser Thr Val Ala Ser Val Ala Thr Phe Val Ser Cys Gly Glu Thr Gly Asp Lys Glu Gly Lys
ACA ATA TCA ACA GTA GCA TCA GTA GCA ACC TTT GTT TCT TGT GGA GAA ACT GAC AAA GAA GGA AAA
              75                            90                       105                    120

FIG. 3/2

| Ile | Ile | Arg | Ile | Phe | Asp | Asn | Ser | Phe | Val | Lys | Asp | Arg | Gln | Ala | Glu | Ile | Lys | Ala | Lys | Asn |
|---|---|---|---|---|---|---|---|---|---|---|---|---|---|---|---|---|---|---|---|---|
| ATA | ATA | AGA | ATT | TTT | GAT | AAT | TCT | TTT | GTT | AAA | GAT | AGA | CAA | GCA | GAA | ATA | AAA | GCA | AAA | AAC |
| 135 | | | | | 150 | | | | | 165 | | | | | 180 | | | | | 195 |

| Phe | Asp | Phe | Asn | Thr | Val | Leu | Leu | Thr | Ala | Gly | Gly | Thr | Val | Gln | Asp | Lys | Ser | Phe | Asn | Gln | Ser |
|---|---|---|---|---|---|---|---|---|---|---|---|---|---|---|---|---|---|---|---|---|---|
| TTT | GAC | TTT | AAC | ACA | GTT | TTA | TTA | ACA | GCA | GGC | GGA | ACT | GTA | CAA | GAC | AAA | TCA | TTT | AAT | CAA | TCA |
| 210 | | | | | 225 | | | | | 240 | | | | | 255 | | | | | | |
| | | | | | | | | | | RsaI | | | | | | | | | | | |

| Ile(Trp) | Glu | Ala | Val | Leu | Glu | His | Tyr | Asp | Gln | Ile | Glu | Lys | Thr | Thr | Asn | Leu | Asp | Arg | Val | Ser |
|---|---|---|---|---|---|---|---|---|---|---|---|---|---|---|---|---|---|---|---|---|
| ATT | TGA | GAA | GCT | GTT | TTA | GAG | CAT | TAT | GAT | CAA | ATA | GAA | AAA | ACA | ACT | AAT | CTT | GAT | AGA | GTT | TCA |
| 270 | | | | 285 | | | | | 300 | | | | | 315 | | | | | 330 | |
| | | | | | | | | | BclI/Sau3A | | | | | | | | | | | |

| Gln | Glu | Thr | Asn | Asn | Gln | Ser | Glu | Leu | Ile | Gly | Lys | Tyr | Lys | Asn | Phe | Leu | Asn | Gly | Asn | Lys | Asn |
|---|---|---|---|---|---|---|---|---|---|---|---|---|---|---|---|---|---|---|---|---|---|
| CAA | GAG | ACT | AAT | AAT | CAA | TCT | GAA | CTT | ATT | GGT | AAG | TAC | AAA | AAT | TTT | TTA | AAT | GGA | AAT | AAA | AAT |
| 345 | | | | | 360 | | | | | 375 | | | | | 390 | | | | | | |
| | | | | | | | | | | RsaI | | | | | | | | | | | |

FIG. 3/3

```
    Val(Trp)Ile Leu Thr Gly Phe Gln Gln Gly Phe Pro Lys Phe Leu Lys Gln Thr Asp Ser
    GTT TGA ATT TTA ACC GGT TTT CAA CAA GGA CAA GAA TTT CCA AAG TTT TTA AAA CAA ACC GAT TCT
    405                    HpaII        420                    435                    450                    HinfI Asn Gly Lys Lys Tyr Ser Asp Leu Leu Ala Glu Lys Lys Val Ile Ile Val Ala Val Asp(Trp)Asp
    AAT GGT AAA AAA TAC AGC GAT TTA GCA GAA AAA AAA GTC ATA ATA GTT GCA GTA GAT TGA GAT
    465                    480                    495                    510                    525

Leu Ser Lys Glu Asp Lys Asp Leu Ile Lys Ala Gly His Phe Ile Ser Leu Leu Tyr Lys Thr Glu
    TTA TCA AAA GAA GAT AAA GAT TTA ATT AAA GCA GGA CAC TTT ATT TCA TTA CTA TAT AAA ACA GAA
    540                    555                    570                    585
```

FIG. 3/4

```
Glu Ala Gly Phe Ile Ala Gly Tyr Ala Ser Ser Lys Phe Leu Ala Tyr Lys Phe Pro Asn Asp Glu
GAA GCA GGT TTT ATT GCA GGG TAT GCG TCG TCT AAA TTT TTA GCA TAT AAA TTC CCA AAT GAT GAA
600                     615                    630                    645                    660

Ala Lys Arg Thr Ile Ala Pro Phe Gly Gly His Gly Val Thr Asp Phe Ile Ala Gly
GCA AAA AGA ACT ATT GCT CCA TTT GGT GGA CAC GGA GTT ACT GAC TTT ATA GCG GGA
        675                    690                    705                    720

Phe Leu Ala Gly Ile Ala Lys Tyr Asn Asn Asp Asn Pro Thr Ala Lys Val Thr Ile Ser Asp Asn
TTT TTA GCA GGA ATA GCA AAG TAT AAC AAT GAC AAT CCA ACC GCT AAA GTA ACA ATT TCA GAT AAT
        735                    750                    765                    780

Asn Ile Asn Ile Asp Thr Gly Phe Ile Ser Asn Asp Lys Thr Ala Thr Phe Ile Asn Gly Ile Val
AAT ATT AAC ATT GAT ACA GGT TTT ATT TCT AAT GAT AAA ACA GCT ACA TTT ATT AAT GGA ATA GTA
795                    810                    825                    840                    855

Asn Lys Ser Ser Leu Val Leu Pro Val Val Gly Ser Leu Thr Ser Ser Val Val Asp Ala Ile Lys
AAT AAA TCT TCA CTT GTT TTA CCA GTG GTA GGT TCA TTA ACT AGC GTG GAT GCA ATA AAA
870                    885                    900                    915
                                              DdeI
```

FIG. 3/4

```
Lys Ser Asn Lys Asp Thr Lys Tyr Leu Ile Gly Val Asp Thr Asp Gln Ser Lys Ile Phe Pro Pro
AAA TCA AAT AAA GAC ACA AAA TAC TTA ATA GGT GTA GAC ACA GAT CAA TCA AAA ATT TTT CCC CCT
           930                   945                   960            975              990
                                                      AccI         Sau3A

Ala Thr Val Phe Phe Thr Ser Ile Glu Lys His Leu Gly Arg Thr Ile Tyr Glu Val Leu Thr Asp
GCT ACA GTC TTT TTC ACA TCA ATA GAA AAA CAT TTA GGA AGA ACC ATT TAC GAA GTC TTA ACT GAT
           1005                  1020                  1035                    1050

Ile(Trp)Leu Lys Lys Glu Asp Ser Lys Phe Leu Gly Ser Phe Arg Ser Phe Lys Leu Thr Asn Pro
ATT TGA CTA AAA AAA GAA GAT TCT AAA TTT TTA GGT TCA TTT AGA TCA TTC AAG TTA ACA AAT CCA
       1065                  1080                  1095                   1110
                             HinfI                      Sau3A         HpaI/HincII Ala Asn Ala Thr Val Tyr Lys Gly Ile Ser Asp Asp Phe Val Gly Val Ser Asn Ser Thr Val Ala
GCA AAC GCT ACA GTT TAT AAA GGA ATT TCA GAT GAT TTC GTT GGT GTT TCT AAT TCT ACA GTT GCA
       1125                 1140                  1155                  1170              1185
```

FIG. 3/5

```
Asp Ala Asp Lys Val Lys Ala Gln Glu Phe Leu Asn Glu Ala Thr Ala Asp Phe Lys Lys Gln Ile
GAT GCA GAT AAA GTA AAA GCA CAA GAA TTT TTA AAT GAA GCT ACA GCA GAT TTT AAA AAA CAA ATT
        1200                    1215                    1230                    1240
                                                         RsaI

Gln Ala Asn Pro Thr Asn Tyr Lys Ser Val Leu Gly Ile Pro Thr Met Leu Ile Asn Asp Asn Asp
CAA GCC AAT CCA ACA AAT TAC AAA AGT GTT TTA GGT ATT CCT ACA ATG TTA ATT AAT GAT AAT GAT
        1260                    1275                    1290                    1305                1320

Ala Lys Asp Asn Glu Lys Ala Leu Asn Glu Leu Ile Lys Lys Ile Asn Gly Thr Thr Thr Thr Thr
GCA AAA GAT AAT GAA AAA GCT TTA AAC GAA TTA ATT AAA AAA ATT AAC GGA ACA ACT ACT ACA ACA
        1335                    1350                    1365                    1380
              HindIII
```

FIG. 3/6

ALA ...3' UNTRANSLATED
GCA TAA TAT CTA TTC ATA GAT AGA TAG AAA TTC AAC AAT AAT TTA AAA ACA ACA TAG CAA CCC AAA
1395                      1410                      1425                      1440

TCA AGG TGT TGT TTT TAA TTC GAA ATA TTA CAA AAA TAA TAT AAT TAT TTA ATA TCT CAA TAG CAA
1455                      1470                      1485                      1500
                          AsuII/TaqI

TAA TAG CAG AAT ATA ATC CTT TTC ATA ATG GTC ATA TTT ATC AAC TAA ATT ATG TTA AAA AAC ATT
1515                      1530                      1545                      1560                      1575

TTC CAA ATG AAA AAA TTG TTG TAA TCT TAA GCG GAA AAT ATA CTC AAA GAG GTG AGT TGG CAG TAG
1590                      1605                      1620                      1635

CTG ATT TTG AAA CTA GAA AAC AAT TTG CTT TAA AAT TTG GAG CAG ATG AAG TTA TAA ATT ACT TTA
1650                      1665                      1670                      1695                      1710

ATA TGC A

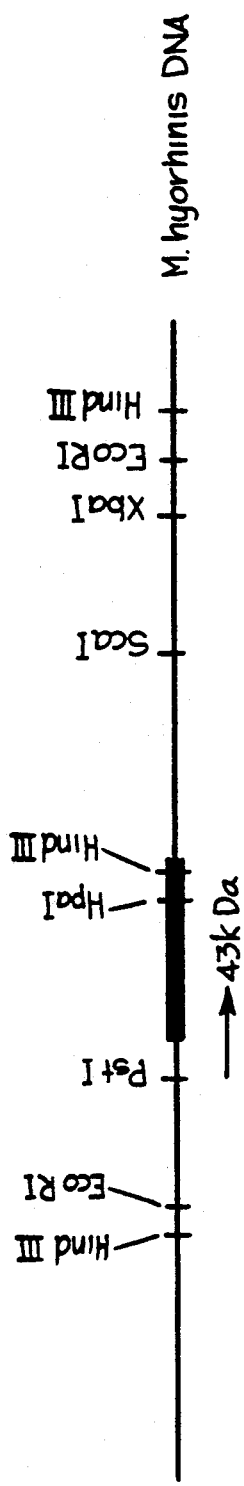
FIG. 4B
FIG. 4C

CLONING OF THE 38KD *MYCOPLASMA HYORHINIS* REGRESSION-ASSOCIATED ANTIGEN

This is a continuation-in-part of U.S. patent application Ser. No. 07/131,815, filed Dec. 11, 1987 (now abandoned) and of U.S. patent application Ser. No. 07/097,910 filed Sep. 16, 1987 (now abandoned), which is a continuation-in-part of U.S. patent application Ser. No. 07/138,923 filed Jan. 4, 1988 (now abandoned), which is a continuation-in-part of U.S. patent application Ser. No. 06/837,494 filed Mar. 7, 1986 now U.S. Pat. No. 4,748,112.

BACKGROUND

The present invention pertains in general to antigens associated with tumors and uses therefor, and in particular to regression-associated antigens (RAAs), to recombinant methods for producing RAAs in *E. coli*, to preparations containing RAAs and to uses for such antigens and preparations.

One approach to diagnosis and treatment of cancers involves the development of polyclonal and monoclonal antibodies against tumor-associated antigens. In almost all reported cases, the immunogens used to obtain antibodies directed against tumor cell components are intact tumor cells or are membrane proteins obtained from the cells.

Early work in this field involved the identification of onco-fetal antigens and blood group antigens [Springer, *Science*, 224, 1198 (1984)] which are expressed by malignant cells and shed into the bloodstream in some instances. Antigens associated with tumor cells may be identified by immunoblotting methods. Du Bois et al., *J. Immunol. Methods*, 63, 7 (1983).

In particular, monoclonal antibodies reactive with the surface of human breast carcinoma cells may be generated and characterized using membrane-enriched fractions of metastatic carcinoma lesions. Schlom et al., *Cancer*, 54 (11 Suppl.), 2777–2794 (1984). One monoclonal antibody is reported to react with a 220,000 to 400,000 dalton high molecular weight glycoprotein complex found in 50% of human mammary carcinomas and 80% of human colon carcinomas. Scholm et al., supra. Mouse monoclonal antibody L6 is reported to recognize a ganglioside antigen that is of particular interest because it is expressed at the surface of cells from most human carcinomas of lung, breast, colon and ovary, while it is present in only trace amounts at the surface of normal cells. Hellstrom et al., *Cancer Res.*, 46, 3917–3923 (1986).

A number of other monoclonal antibodies reactive with tumor-associated antigens on the surfaces of other human cancer cells, including ovarian, pancreatic and intestinal malignancies, may thus be obtained. *Proceedings of the UCLA Symposium on Monoclonal Antibodies and Cancer Therapy*, Reisfeld et al., eds., Alan R. Liss, Inc., New York, 3–74, 97–109 and 149–164 (1985).

Monoclonal and polyclonal anti-tumor cell antibodies described to date are directed against determinants of human tumor cell antigens which may elicit an immune response in test animals chosen for the production of tumor-specific antibodies. It is not known whether patients harboring tumors or treated with specific and/or non-specific immune stimulants produce antibodies against these antigenic determinants. Therefore, the relevance of such antibodies in mediating regression of tumors in patients is unclear. Passive transfer of such antibodies generated in animals into patients has met with limited success. Lowder et al., *Western J. Med.*, 143, 810 (1985).

A clinical approach toward active immunotherapy of tumors involves a generalized stimulation of the patient's own immune system using non-specific stimulants such as components of the walls of two bacterial cells, *Mycobacterium bovis* (BCG strain) and *Corynebacterium parvum*, or "detoxified" bacterial endotoxin. In parallel, biological response modifiers such as interleukin-2 may be used to induce activation of the immune system and cause tumor cell destruction. Mule et al., *J. Immunol.*, 135, 646 (1985); and Rosenberg et al., *New Engl. J. Med.*, 313, 1485 (1985).

In an approach called active specific immunotherapy, immunization of cancer patients may be attempted with preparations derived from allogeneic tumor cells (tumor cells obtained from a histopathologically similar tumor of a different patient). This may specifically stimulate the patient's own immune system to possibly unique antigenic structures present on a particular malignant cell type, and may thus induce tumor regression. Lachman et al. *Br. J. Cancer*, 51, 415–417 (1985); and Wallack et al., *Surgery*, 96, 791–800 (1984). Active specific immunotherapy may also be attempted by systematically injecting autologous (autochthonous) tumor cells (i.e., cells derived from the tumor mass of the same patient) intradermally or subcutaneously. Laucius et al., *Cancer*, 40, 2091 (1977).

Various preparations of autologous tumor cells or of allogeneic tumor cell lines have been used in active specific immunotherapy. Key et al., *Adv. Immun. Cancer Ther.*, 1, 195–219 (1985); Weisenburger et al., *J. Biol. Response Mod.*, 1, 57–66 (1982); and Kan-Mitchell et al., *Proceedings of the UCLA Symposium on Monoclonal Antibodies and Cancer Therapy*, supra, 523–536. The preparations are generally treated with irradiation, mechanical disruption, or freeze-thaw cycles to render the tumor cells non-viable. They are then used as immunogens, with or without an adjuvant, and are administered by a variety of routes (such as intradermal, subcutaneous, intramuscular or intralymphatic) for the purpose of immunizing cancer patients. Relatively little toxicity has been reported with these preparations, and encouraging clinical responses have been obtained in significant numbers of advanced cancer patients.

Serum samples may be obtained from patients with documented malignancies that are in the state of tumor progression from the primary site of origin to other locations in the body (metastasis) or by a demonstrable growth of the primary tumor mass. The patients may then be subjected to intralymphatic immunotherapy as described in Juillard et al., *Bull. Cancer*, 66, 217 (1979), using infusions of tumor cells obtained from their own tumors or cultured tumor-derived cells established from malignancies of the same type as the patient in question as described in Juillard et al., *Cancer*, 41, 2215 (1978); and in Weisenburger et al., *J. Biol. Response Mod.*, 1, 57 (1982). The amount of neoplastic cells used for immunization and methods of their processing including washing and irradiation prior to administration into patients is reported. Juillard et al., *Cancer*, 41, 2215–2225 (1978); and Bubbers et al., *Bull. Cancer*, 68, 332–337 (1981). However, such procedures do not identify RAAs or disclose recombinant production of RAAs.

One major limitation of attempts at active specific immunotherapy is the undefined nature of the tumor cell preparations (generally intact irradiated cell suspensions or mechanically disrupted lysates of cells). Cells from autologous tumor cells grown in tissue culture or continuously passaged tumor cell lines may undergo significant changes in their phenotypes during growth in laboratory culture. Reagents or tests to standardize the preparations for their expected potency have not been available. Membrane proteins may be shed from intact irradiated cells and proteins in cell lysates may be degraded by proteolytic enzymes. Different preparations used in attempts at active specific immunotherapy may, therefore, have variable efficacies although similar processes and cell types are utilized. Furthermore, the means of monitoring the immune response of individual patients is not available for tailoring the immunization dose and the immunization schedule for optimal clinical outcome. In addition, it is often the case that autologous tumor cell preparations are not practical because of a lack of an adequate amount of tumor from the patient to be treated.

The results of clinical studies with autologous tumor cell vaccines are encouraging when a potent adjuvant such as BCG is used along with the tumor cell suspension. Hoover et al., *Cancer Res.*, 44, 1671–1676 (1984). Some patients immunized through different routes with allogeneic cells, with or without adjuvants, have shown significant, often dramatic, clinical responses. Weisenburger, *J. Biol. Response Mod.*, 1, 57–66 (1982); Mitchell, in *Proceedings of the UCLA Symposium on Monoclonal Antibodies and Cancer Therapy, supra*, 495–504. Certain key antigen components of tumor cells may be able to elicit protective/regressor antibodies in humans.

Results from a number of animal models support the use of tumor cell components in active specific immunization to induce tumor regression [Key et al., *J. Biol. Response Mod.*, 3, 359–365 (1984); and Srivastava et al., *Proc. Nat'l Acad. Sci. (USA)*, 83, 3407–3411 (1986)]. Neoplasms induced in mice by polycyclic aromatic hydrocarbons such as 3-methylcholoanthrene express individually distinct tumor-associated transplantation antigens. These antigens are immunogenic in their syngeneic hosts and provide transplantation immunity only against their respective tumors and not against independent tumors induced by the same or a different carcinogen or against tumors of viral origin. Transplantation immunity in mice may be elicited by prior growth and removal of tumor transplants or by immunization with irradiated tumor cells, tumor cell membranes or solubilized antigen preparations.

A monoclonal antibody designated PF/2A is a product of standard monoclonal antibody production techniques involving injection into mice of cells of a human squamous lung carcinoma cell line. PF/2A antibody is reported to react with breast carcinoma, colon carcinoma, gastric carcinoma, tumors of ectodermal origin and squamous lung cell carcinomas as well as a 24 kilodalton ("kd") polypeptide extracted from squamous lung cell carcinoma cells [Fernsten et al., *Cancer Res.*, 46, 2970–2977 (June, 1986)]. Monoclonal antibody PF/2A is also reported to immunoprecipitate a 46 kd polypeptide extracted from human cell lines infected with *Mycoplasma hyorhinis* (*M. hyorhinis*), and stains, but to not precipitate, a 24 kd component derived from *M. hyorhinis* [Fernsten et al., *Infect. Immun.*, 55, 1680–1685 (July, 1987)]. However, no association with regression of tumors is shown or suggested for this antibody or antigens reactive with the antibody by Fernsten et al.

In Gussack et al., *Cancer*, 62, 57–64 (1988), it is reported that most primary human carcinomas uniformly express an oncofetal epitope which is reported not to have been demonstrated previously in established human carcinoma cell lines. It is further reported that several low-passage cell lines of human squamous cell carcinoma ("SCC") from head and neck tumors are derived, characterized and examined for expression of a 44 kd polypeptide oncofetal antigen ("OFA") at the cell surface. These new cell lines and two long-term, established SCC lines (FaDu and Detroit 562) are reported to displayed OFA at the cell surface, as determined by flow cytometry using a monoclonal antibody. It is proposed that the expression of a 44 kd OFA is a common feature of human SCC, and that this marker may prove useful in the detection and treatment of these tumors. Nevertheless, no indication is given in Gussack et al. that the proposed 44 kd OFA is a regression-associated antigen.

In Hollinshead et al., *Cancer*, 60, 1249–1262 (1987), the 10-year cumulative experiences of five year survivals of patients entered into a successful phase II specific active tumor-associated antigen ("TAA") immunotherapy trial, a successful phase III specific active immunotherapy trial A and of patients in an unsuccessful specific active immunotherapy trial B are reported. The TAAs used are reported to be lung tumor cell membrane components which produce cell mediated components which produce cell-mediated immunity as measured in vivo and in vitro. In addition, monoclonal antibody-derived epitope enzyme immunoassays are reported using a 37 kd lung squamous cell TAA to monitor specific, early antibody rises in the bloodstream. However, no relationship of the TAAs to regression-associated antibodies is reported.

In Young et al., *Proc. Natl. Acad. Sci. (USA)*, 85, 4267–4270 (1988), it is reported that, to understand the immune response to infection by tuberculosis (*M. tuberculosis*) and leprosy (*M. leprae*) bacilli and to develop improved vaccines, an investigation of the nature of antigens that are involved in humoral and cell-mediated immunity is discussed. Five studied immunodominant protein antigens (three from *M. leprae*, 71 kd, 65 kd and 18 kd; and two from *M. tuberculosis*, 70 kd and 65 kd) are reported to be homologs of stress proteins. It is indicated that this finding and observations with other pathogens suggested that infectious agents may respond to the host environment by producing stress proteins and that these proteins may be important immune targets, so that it is postulated in Young et al. that abundant and highly conserved stress proteins may have "immunoprophylactic" potential for a broad spectrum of human pathogens. Nevertheless, no relationship to tumor regression is disclosed.

In Jessup et al., *Arch. Surg.*, 122, 1435–1439 (1987), the antibody response of patients is reported to be used to characterize autoantigens in human colorectal carcinoma. Primary and metastatic carcinomas with paired normal tissues are reported to be extracted and transferred onto nitrocellulose membranes by the Western transfer technique which are incubated with the serum of the patient from whom the tumor was derived. Autoantigens are reported to be identified by indirect immunoperoxidase staining. All tumors are reported to contain at least one autoantigen. Six tumor-associated autoantigens (reported to have molecular weights of 26 kd, 29 kd, 32 kd, 38 kd, 41 kd and 58 kd are reported to be identified by antibodies in 25% or more of the sera.

Eleven metastases are reported to express a 41 kd autoantigen present in only a third of the extracts of normal liver or lung. Thus, the number of dominant polypeptide autoantigens in colorectal carcinoma is reported to be restricted to six molecules. These autoantigens may be organ-associated antigens that are expressed by neoplastic cells. The 41 kd autoantigen is reported to be a potential marker for metastases. A generic vaccine is reported to appear to be feasible for colorectal carcinoma since the number of dominant antigens is limited. However, no relationship of the autoantigens to regression is reported although it is suggested that autoantibodies to cytoplasmic antigens may be important for the survival of the patient.

In Law et al., *Cancer Res.*, 47, 5841-5845 (1987) is reported the characterization of a 65 kd tumor rejection antigen obtained from a murine malignant melanoma. Greater than 95% inhibition of primary tumor growth in a mouse system is reported for the use of irradiated 591 murine malignant melanoma cells expressing the 65 kd antigen, but the extracted and purified 65 kd antigen from 591 cells is reported to be in effective in inhibiting primary tumor growth in a mouse system. Although a 65 kd melanoma specific tumor rejection antigen from another murine malignant melanoma cell line (B16) is reported to effective in inhibiting tumor growth, no relationship of the reported antigen to regression-associated antibodies is reported.

A knowledge of the antibody response associated with human tumor regression following active specific immunotherapy and identification of subcellular components involved in eliciting such specific antibodies should lead to the development of improved active specific immunogens for cancer immunotherapy. Thus, it is desirable to develop: (i) preparations which will be more enriched in the relevant specific immunogens; (ii) reagents to screen better cell sources and quantitate the immunogens in preparations derived from these cells such that different preparations may be meaningfully standardized; and (iii) assay methods to monitor patients' specific immune response to these immunogens, thereby providing the physician an ability to adjust the treatment protocol in order to produce a better clinical outcome.

SUMMARY OF THE INVENTION

Regression-associated antigens may be identified based upon their reactivity with regression-associated antibodies (RAAbs), which antibodies are produced in patients undergoing active immunization and responding with tumor regression.

RAAbs according to the present invention may be detected by obtaining a first sample of serum from a patient diagnosed as not being in a state of regression and then obtaining a second sample of serum from the patient after diagnosis as being in a state of regression. Protein extracts of a neoplastic cell are exposed to each of the samples. The formation of an immune complex between a component of the neoplastic cell and an antibody in the second serum sample and the absence of such a complex with an antibody in the first serum sample is indicative of the presence of RAAbs in the second sample.

The present invention comprehends regression associated antigens encoded by DNA from a mammalian cell line which may have an infection with or be transformed with DNA of *Mycoplasma hyorhinis*, ("*M. hyorhinis*") and regression associated antigens encoded by DNA of *M. hyorhinis*.

The present invention provides the purification and a partial amino acid sequence analysis of two distinct molecular entities, a 38 kd and a 43 kd protein, from cultured *M. hyorhinis* and the demonstration that these two proteins are reactive with human regression-associated antibodies. The present invention involves the isolation and partial characterization of *M. hyorhinis* DNA sequences which encode all or part of the 38 kd antigen and the 43 kd antigen and the production of these proteins from cultured *M. hyorhinis* and from mammalian cells infected with *M. hyorhinis*, and the production of these antigens from genetically engineered microbial or mammalian cells containing *M. hyorhinis* gene sequences which encode the 38 kd and/or the 43 kd RAAs. The *E. coli* recombinantly-produced regression-associated antigen is more preferably greater than or equal to 95% pure as determined by reducing SDS PAGE analysis followed by Coomassie staining.

In particular, the present invention provides methods and materials for expressing RAAs recombinantly. Specifically, the 38 kd and 43 kd antigens according to the present invention are provided as method using isolated DNA and vectors in *E. coli*. The present invention provides method for purifying these RAAs as expressed in *E. coli*.

Immunotherapy may be performed according to the present invention exposing to the immune system of a patient by introducing into a bodily fluid an RAA according to the present invention, *M. hyorhinis*-derived protein preparations containing the 38 kd or the 43 kd antigen or protein preparations containing 38 kd and/or 43 kd antigen derived from genetically engineered cells containing a gene encoding the 38 kd or the 43 kd antigen or any portion thereof which includes an epitope. Such protein preparations may be exposed to the immune system of a patient by introducing them into the lymphatic or hematic fluid (i.e., the lymph or blood) or into tissues of a patient (e.g. by intramuscular or subcutaneous injection). The response of a patient to immunotherapy may be monitored for symptoms and signs associated with a neoplasm and by determining a circulating level of RAAbs in a patient.

The present invention also provides monoclonal or monospecific polyclonal antibodies exhibiting a specific immunoreactivity with an RAA. An antibody according to the present invention may be purified by contacting a substrate bound RAA with a solution containing an RAAb and eluting the RAAb from the RAA.

A monoclonal or monospecific polyclonal antibody directed against one or more of the RAAs of the present invention may be used in radioimmunoassays, enzyme-linked immunoadsorbent assays or direct or indirect immunohistochemical assays to determine the presence and the levels of one or more RAAs in tumor biopsy specimens or in body fluids. Such an antibody may also be administered to cause direct antibody-dependent tumor cell cytotoxicity ("ADCC") or complement-dependent tumor cell cytotoxicity ("CDCC"). Alternatively, such an antibody may be bound to a bioactive moiety, including but not limited to anticancer drugs, such as toxins, radioisotopes, chemotherapeutic substances, or cell growth and differentiation regulators (e.g., IL-1, TGF-$\beta$, TNF, IFN and the like), and introduced into a bodily fluid of a patient so that the bioactive moiety is preferentially delivered to tumor cells by the specificity of the drug-bound antibody for the tumor cell. Such approaches may be useful in the in vivo diagnosis of or in the therapy of malignancies.

The present invention also provides a regression-associated antigen encoded by a purified and isolated nucleic acid described by a nucleotide sequence selected from the group consisting of: the nucleotide sequence as shown in FIGS. 1 or 3; a nucleotide sequence which encodes the same sequence of amino acids as encoded by the nucleotide sequence shown in FIGS. 1 or 3; and a nucleotide which encodes an epitope encoded by 18 sequential nucleotides in the nucleotide sequence shown in FIGS. 1 or 3. The present invention also provides a monoclonal or monospecific polyclonal antibody exhibiting a specific immunoreactivity with such an antigen.

A purified and isolated nucleic acid according to the present invention may be described by a nucleotide sequence selected from the group consisting of: the nucleotide sequence as shown in FIGS. 1 or 3; a nucleotide sequence which encodes the same sequence of amino acids as encoded by the nucleotide sequence shown in FIGS. 1 or 3; a nucleotide sequence which hybridizes with any 20 sequential nucleotides as shown in the nucleotide sequence shown in FIGS. 1 or 3 or in the complement thereto; a nucleotide sequence which would hybridize with any 20 sequential nucleotides as shown in the nucleotide sequence shown in FIGS. 1 or 3 but for the redundancy of the genetic code; and a nucleotide sequence which encodes an epitope encoded by 18 sequential nucleotides in the nucleotide sequence shown in FIGS. 1 or 3. The present invention also provides a ell transformed with such a nucleic acid, and an expression product of such a cell.

The present invention further provides a purified and isolated nucleic acid described by a restriction map shown in FIG. 2, a cell transformed with such a nucleic acid, and an expression product of such a cell, as well as a monoclonal or monospecific polyclonal antibody exhibiting a specific immunoreactivity with the expression product.

A method of in vivo imaging according to the present invention includes injecting an RAAb into a patient, the antibody being bound to a radioisotope, and scanning the patient using radioisotope scanning, or injecting an RAAb into a patient, the antibody being bound to a heavy metal, and scanning the patient using magnetic resonance scanning.

A method for isolating a regression-associated antigen from *M. hyorhinis* according to the present invention includes extracting protein from cells of *M. hyorhinis*, separating from the cells a regression-associated antigen encoded by a purified and isolated nucleic acid described by a nucleotide sequence selected from the group consisting of: the nucleotide sequence as shown in FIGS. 1 or 3; a nucleotide sequence which encodes the same sequence of amino acids as encoded by the nucleotide sequence shown in FIGS. 1 or 3; a nucleotide sequence which encodes an epitope encoded by 18 sequential nucleotides in the nucleotide sequence shown in FIGS. 1 or 3; and a purified and isolated nucleic acid described by a restriction map shown in FIG. 2.

The present invention further provides an immortalized cell line producing a monoclonal antibody to a regression-associated antigen. A cell line secreting an I$_g$M antibody which may be directed to a regression-associated antigen is the cell line designated as ATCC Deposit No. HB 9540. A monoclonal antibody secreted by the cell line designated ATCC Deposit No. HB 9540 is also provided by the present invention.

An immunoassay kit according to the present invention includes a regression-associated antibody and may further include a regression-associated antigen. Alternatively, an immunoassay kit according to the present invention may include a regression-associated antigen in the absence of a polyclonal or monoclonal regression-associated antibody.

A method of passive immunization according to the present invention involves injection into a patient of a regression-associated antibody.

The present invention also provides a regression-associated antigen encoded by a purified and isolated nucleic acid described by a nucleotide sequence selected from the group consisting of: a nucleotide sequence which encodes the sequence of amino acids Ser-Gly-Glu-Thr-Asp-Lys-Glu-Gly-Lys-Ile-Arg-Phe-Asp-Asn-X-Phe-Val-Lys-Asp wherein X may be Cys or Ser; a nucleotide sequence which would hybridize with any 20 sequential nucleotides encoding Ser-Gly-Glu-Thr-Asp-Lys-Glu-Gly-Lys-Ile-Arg-Phe-Asp-Asn-X-Phe-Val-Lys-Asp wherein X may be Cys or Ser but for the redundancy of the genetic code; and a nucleotide sequence which would hybridize with any 20 sequential nucleotides as shown in the nucleotide sequence encoding Ser-Gly-Glu-Thr-Asp-Lys-Glu-Gly-Lys-Ile-Arg-Phe-Asp-Asn-X-Phe-Val-Lys-Asp wherein X may be Cys or Ser; and a nucleotide sequence which encodes an epitope encoded by 18 sequential nucleotides in the nucleotide sequence encoding Ser-Gly-Glu-Thr-Asp-Lys-Glu-Gly-Lys-Ile-Arg-Phe-Asp-Asn-X-Phe-Val-Lys-Asp wherein X may be Cys or Ser.

A process for purifying a regression-associated antigen includes the steps of applying a regression-associated antigen to an anion exchange column; collecting the flow-through fractions containing a regression-associated antigen from the anion exchange column; binding the regression associated antigen to an affinity chromatography column; eluting the regression-associated antigen from the affinity chromatography column; and retaining the purified regression-associated antigen.

The process may also include the steps of introducing the regression-associated antigen into a cation exchange column; and removing the regression-associated antigen from the cation exchange column by elution.

BRIEF DESCRIPTION OF THE DRAWINGS

FIG. 1 is a restriction map, nucleotide sequence and deduced amino acid sequence for a gene encoding the 38 kd RAA of *M. hyorhinis* and containing an 18 mer probe sequence and a 26 mer probe sequence according to the present invention;

FIG. 3 is a restriction map, nucleotide sequence and deduced amino acid sequence for a gene encoding the 43 kd RAA of *M. hyorhinis;*

FIG. 4A is a restriction map of a *M. hyorhinis* DNA fragment containing the gene encoding a 43 kd protein of *M. hyorhinis;*

FIG. 4B is a restriction map of a clone designated pMu3-8 which contains sequences encoding the N-terminal region of the 43 kd RAA;

FIG. 4C is a restriction map of a clone designated pMu3-1 containing sequences encoding the 43 30 kd RAA and sequences 3' and 5' to the coding sequence; the DNA fragments in pm43-8 and pM43-1 contain the homologous restriction sites found in the corresponding DNA segment indicated in FIG. 4A;

DETAILED DESCRIPTION

Figure 2A:
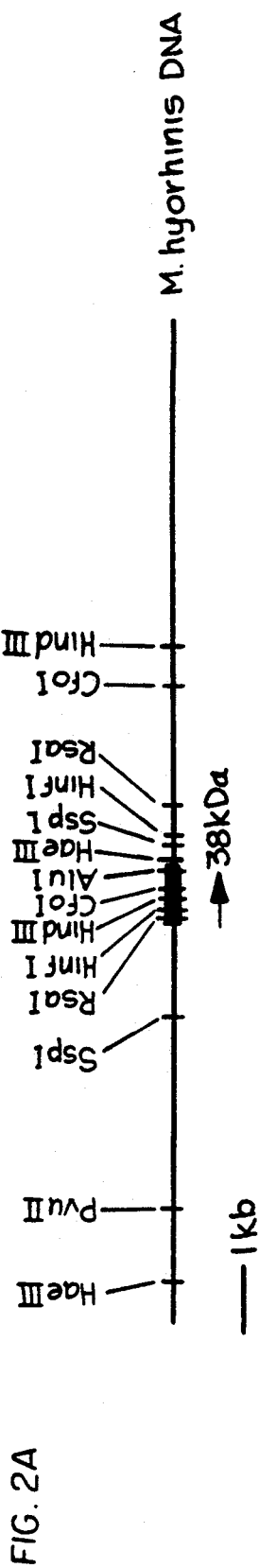
FIG. 2A is a restriction map of a gene encoding a 38 kd protein of *M. hyorhinis;*

The present invention relates to the identification of human tumor cell-associated antigens and antibodies developed against such antigens in patients responding with tumor regression following active specific immunotherapy using tumor cells or cell extracts. These novel antigens, designated herein as RAAs, may be detected using RAAbs from patient sera in a number of fresh human tumor extracts and in cultured human tumor cell lines.

In particular, the present invention provides a 38 kd and a 43 kd RAAs from mycoplasma DNA by expression from *E. coli.* The 38 kd and 43 kd proteins thus produced are purified to be greater than or equal to 95% pure as determined by reducing SDS-PAGE analysis followed by cosmassie staining and are face of other mycoplasma or human proteins.

Discrete antigens associated with cultured human tumor cells may be identified by screening large numbers of monoclonal antibodies produced in mice and other animals against tumor cells or partially fractionated immunogens derived therefrom. However, most antibodies directed against such antigens may not be associated with the progression or regression of tumors and, as such, the antigens detected by these antibodies are unlikely to have therapeutic potential as active immunogens. Furthermore, human antigenic determinant(s) which elicit an antibody response in mice or other animals might not trigger human immune surveillance mechanisms against a tumor.

In the present invention, specific antibodies have been detected in sera from patients undergoing tumor regression following active immunization by intralymphatic infusion of cells derived from their own tumors (autochthonous) or established tumor-derived cell cultures of similar histopathologic type (allogeneic). The antibodies of this invention are characterized by their specific reactivity toward certain antigens associated with certain human tumor cells. These antibodies have thus been used to identify specific antigens in tumor cells and tissues. These tumor-associated antigens, designated herein as RAAs, may be further grouped based upon their sizes, their ability to react with RAAbs from patients regressing different malignancies, and their presence and/or their relative abundance in cells obtained from different types of human cancer.

Partial tumor regression is indicated if the following is observed: stabilization of a tumor which was progressing prior to immunotherapy (i.e., failure to detect any objective change in tumor size for three months), or less than fifty percent decrease in tumor size and associated subjective improvement or status quo. Such stabilization of tumor growth is associated with the development of delayed hypersensitivity to immunogens in the irradiated neoplastic cells used for treatment and is assessed by subcutaneous and intradermal skin testing of the cellular preparations.

A successful tumor regression response is defined as an objectively measurable decrease (i.e. at least fifty percent) in the size of the tumor mass. Tumor mass is assessed by direct measurement, when the tumor is near the surface of the body and directly palpable, by radiological measurements and by the additional criteria cited above.

Serum samples are obtained from patients before and at different times after initiation of the immunotherapy. The status of the tumor is assessed as described above. The serum samples from patients undergoing the immunotherapy regimen and responding with tumor regression are tested along with the serum samples from each patient obtained prior to the initiation of immunotherapy and/or before the patient is in a state of regression.

RAAbs according to the present invention are antibodies which are induced in response to administration of irradiated tumor cell immunogens and are associated with the stabilization or regression of tumor masses.

RAAs according to the present invention include antigens present on human tumor cells which presumably induce the production of RAAbs and which thus may be recognized by antibodies in the sera of patients showing tumor regression in response to tumor cells administered through the intralymphatic route by comparison to less or no recognition by antibodies in the sera prior to regression. Polyclonal or monoclonal antibodies against RAAs may be prepared in animals and may be used for therapeutic purposes, diagnostic tests or monitoring the course of therapy, including therapy involving active immunization protocols.

The specific RAAs of this invention are distinguishable from one another and also from other antigens associated with tumors and cells derived from tumors based upon their sizes and immunological properties. See Hood et al., *Immunology,* Bejamin/Cummings Publishing Co., 510–529 (1984); and Sell, in *Proceedings of the UCLA Symposium on Monoclonal Antibodies and Cancer Therapy, supra,* 3–21 (1985). Carcinoembryonic antigen (CEA) is much larger than any of the RAAs, as are several of the antigenic determinants which may be identified with existing murine monoclonal antibodies. Human chorionic gonadotropin (HCG) consists of two subunits both of which are distinguishable from RAAs in a reducing SDS-PAGE system (the $\beta$ subunit of HCG is 35 kd in size and its $\alpha$ subunit is 16 kd in size [Pierce et al., *Ann. Rev. Biochem.,* 50, 465–495 (1981)]).

There is a rapidly growing list of tumor-specific antigens identified with murine monoclonal antibodies. The available information distinguishes these antigens from RAAs of this invention on the basis of size or relatedness to normal cellular constituents (*Monoclonal Antibodies and Cancer Therapy*, Reisfeld et al, eds., supra). The availability of monoclonal antibodies has lead to the detection of a 92 kd, a 23 kd, and a 17 kd antigens in urinary bladder cancer, Ben-Aissa et al., *Br. J. Cancer*, 52, 65–72 (1985). However, these monoclonals do not react with melanoma cells (the principal source of the 19 kd to 23 kd RAA described herein).

A monoclonal antibody specific for a 43 kd surface protein of human leukemia cell line (THP-1) cross-reacts with the intermediate filament vimentin found in normal cells. Herman et al., *J. Cell Sci.*, 73, 87–103 (1985). A 52 kd protein is released by human breast cancer cells [Capony et al., *Biochem. Biophys. Res. Commun.*, 108, 8–15 (1982)], and a high molecular weight glycoprotein (220 kd to 400 kd) as well as a 90 kd protein are found in membranes of human breast cancer [Schlom et al., *Cancer*, 54, 2777–2794 (1984)]. A sarcoma-specific 70 kd antigen appears to be different from an according to the present invention that the sarcoma 70 kd antigen was not detectable in carcinoma cell lines [Feit et al., *Cancer Res.*, 44, 5752–5756, (1984)].

RAAs or proteins containing certain antigenic determinants present in RAAs may be encoded by the DNA of *M. hyorhinis* and may therefore, be isolated from cultured *M. hyorhinis* or cells expressing *M. hyorhinis* genes encoding such proteins.

Mycoplasma infection of mammalian cell lines is known to result in changes in cellular metabolism and function. Van Diggelen et al., *Exp. Cell Res.*, 106, 191 (1977); and Van Diggelen et al., Cancer Res., 37, 2680 (1977). In addition, mycoplasmas tend to be strongly adherent to the surfaces of mammalian cells and would be present in soluble and particulate extracts from washed cells. Butler et al., *Infect. Immun.*, 42, 1136 1983). Because of the suspected presence of *M. hyorhinis* in the A375 melanoma cell line (ING-A) deposited on Feb. 12, 1987, under the accession number ATCC CRL 9321, with the American Type Culture Collection, 13201 Parklawn Drive, Rockville, Maryland 20852, and all other RAA-positive cell lines, the involvement of this microorganism in the production of RAAs either encoded for in the *M. hyorhinis* genome or through induction of expression of RAAs in the host human tumor cells is a legitimate possibility for experimental determination.

Several procedures are generally useful for characterizing RAAs, RAAbs or constitute applications for RAAs and RAAbs. These procedures include: immunoblotting, preparation of plyclonal RAAbs, production of monoclonal antibodies, targeting drugs to a tumor, diagnostic in vivo imaging using labelled RAAbs, and "Dot Blot" immunoassays for RAAs.

In a typical Western immunoblotting procedure as described in Towbin, et al., *Proc. Nat'l Acad. Sci (USA)*, 76, 4350 (1979), total cell protein extracts or subcellular fractions are subjected to reducing sodium dodecyl sulfate-polyacrylamide gel electrophoresis (SDS-PAGE). The proteins are transferred by electroelution into nitrocellulose filters which are subsequently incubated with appropriate dilutions of the test serum or antibody preparation. After the incubation of the filter with antibody and extensive washing, the filter is incubated with $I^{125}$-labeled Protein A of *Staphylococcus aureus* (which specifically binds to the Fc region of antibody molecules), washed to remove unbound Protein A and exposed to X-ray film for autoradiography. Each radioactive band represents the location of a protein species which formed an immune complex with antibodies from the test sera.

Serum samples from patients undergoing immunotherapy may be tested to monitor titers of RAAbs in patients regressing tumors after intralymphatic immunotherapy using immunoblotting of various recombinant produced RAAs. Various dilutions of sera samples from each patient are evaluated for the ability to detect one or more of the specific size RAAs. The assay for the quantitation of RAAb titer may also be used in monitoring the effects of drugs on patients undergoing immunotherapy.

Antisera may be specifically produced by immunizing rabbits with injections of purified RAAs according to the present invention as follows. A first inoculation may contain membranes or soluble RAAs (purified from solubilized membranes or from conditioned medium) with Freund's incomplete adjuvant or with alumdsorbed tetanus toxin as an adjuvant. Succeeding inoculations may contain the RAA and Freund's incomplete adjuvant. The animals are bled to obtain sera. Polyclonal antibodies may be isolated from the sera by conventional techniques known in the art, *Handbook of Experimental Immunology*, Vol. 3, Weir, ed., A 3.1 to A 4.10, Blackwell Scientific Publications (1978). Alternately, affinity columns containing purified RAAs bound to Affi-gel 10 TM (Bio-Rad) may be prepared using supplier's instructions. Highly specific polyclonal antibodies may be prepared using this affinity column by conventional procedures. *Affinity Chromatography*, 41–44 and 92–95 Pharmacia AB, Uppsala, Sweden. High-titer i.e., greater than 1:10,000) rabbit antisera specific for 38 kd and 43 kd human RAAs have been produced, with sera from a rabbit.

Monoclonal antibodies according to the present invention may be produced according to the procedure of Kohler et al., *Nature*, 256, 495 (1975) with the substitution of a preparation of an RAA for an antigen employed therein.

Basically, monoclonal antibodies are produced by injecting mice with immunizing doses of RAAs, as described above for rabbit immunization. Spleens are removed from the immunized animals, and spleen cells are fused to myeloma cells using a fusogen, such as polyethylene glycol. Hybridoma cells producing monoclonals are selected for in a selective growth medium such as the conventional HAT medium. Monoclonal antibodies specific for RAAs may be isolated by chromatography from media in which such hybridomas have been cultured, Brown et al., *J. Immunol.*, 131, 180–185 (1981).

Proteins characterized by immunoblotting using known RAAbs and those preparations reacting positively with one or more of the RAAbs may be employed to actively immunize a patient as part of a therapeutic regimen.

Drugs may be targeted to a tumor according to the present invention. An anti-cancer drug may be bound to a monoclonal antibody against an RAA (i.e., a monoclonal RAAb). Such antibody-mediated drug delivery systems are reviewed in Rodwell et al., *Biotechnology*, 3, 889–894 (1985).

By introducing a monoclonal antibody specific for an RAA and linked to an anticancer drug into a bodily fluid (blood, lymph or any other appropriate fluid such as cerebrospinal, etc.) of a patient, such a drug may be selectively delivered to tumor cells expressing an RAA for which the monoclonal RAAb is specific. It is anticipated that such binding of a tumor cell with an anticancer drug will preferentially exert an adverse effect on its survival.

Diagnostic in vivo imaging of malignancies using high titer polyclonal or monoclonal RAAbs coupled to a radioisotope (e.g., $I^{131}$, $^{90}Y$, $^{111}In$) or heavy metal (e.g., albumin-coated magnetite, $Fe_3O_4$) may be achieved using radioisotope or magnetic resonance scanning after administration to the patient of the coupled RAAb [Lauterbur, P. C., 47–57, in *Accomplishments in Cancer Research* 1985, Fortner et al., eds., J. B. Lippincott Co., 1986; Weinstein et al., pages 473–487, in *Monoclonal Antibodies and Cancer Therapy*, Reisfeld and Sell, editors, A. R. Liss, Inc., New York 1985].

In a "Dot Blot" immunoassay for RAAs, a grid of 1.5 cm × 1.5 cm squares are drawn on 0.45 micron pore size nitrocellulose filter paper (Schleicher and Schuell, Inc., Keene, N.Y.). The paper is rinsed in distilled water for 5 minutes and allowed to air dry. A 20 µl sample of a test extract presumed to contain an unknown amount of RAAs is mixed with an equal volume of 0.05M Tris HCl (pH 7.4) 0.28 M NaCl, 1.4% Triton X-100 ®, and 0.2% SDS, and heated to 100° C. for 5 minutes. The sample is centrifuged at 10,000 × g and the supernatant is spotted with a micropipet within a square on the nitrocellulose filter. The filter is dried and then fixed for 15 minutes in a solvent containg 10% acetic acid and 25% isopropanol with constant agitation; this is followed by several rinses in water. The filter is then processed according to the immunoblotting technique described above, with the exception that a one hour incubation with goat anti-human antibody conjugated to horse radish peroxidase (1:2000) is substituted for the incubation with radioiodinated Staphylococcus protein A. After this one hour incubation and washing according to the immunoblot procedure, the individual squares of nitrocellulose are cut out and placed into individual wells of a multiwell plate (Costar, Cambridge, Mass.). Staining solution is added to each well in the amount of 0.5 ml of phosphate-buffered saline or isotonic citrate buffer (pH7) containing 0.6 mg/ml of o-phenylenediamine dihydrochloride supplemented with 1 µl of 30% hydrogen peroxide. The solution with the filter square is incubated in the dark for 30 minutes and color formation is stopped by adding 0.5 ml 4 N $H_2SO_4$ per well. Absorbance is then measured in a spectrophotometer at 490 nm. This assay provides a linear quantitation of RAAs when increasing amounts RAAs are spotted onto the nitrocellulose filter paper.

EXAMPLE 1

NH$_2$-Terminal and Internal Amino-Acid Sequence Analysis of 38 kd Antigen

*Mycoplasma hyorhinis* (ATCC No. 23839) was cultured in a medium containing the following ingredients: 2.1% PPLO broth (DIFCO Laboratories, Detroit, Mich.), 0.25% yeast extract, 0.5% glucose, 20% fetal calf serum, 100 units/ml penicillin, 100 µg/ml streptomycin. Twenty-five milligrams of *M. hyorhinis* protein was harvested by centrifugation as a washed bacterial pellet, and membrane bound hydrophobic proteins were isolated by solubilization of *M. hyorhinis* with 4 ml of phosphate buffered saline containing 2% Triton X-114 ™ for 4 hours at 4° C.

Insoluble components were removed by centrifugation at 4° C. for 10 minutes at 10,000 × g, and TX-114 ™ soluble material was incubated for 5 minutes at 37° C. to induce condensation of Triton X-114. The resulting cloudy suspension was centrifuged at 10,000 × g for 10 minutes at 22° C. The aqueous phase was removed by aspiration, the detergent phase was brought to the original volume with PBS, and the phase separation procedure, as described above, was repeated. The TX-114 ∩ phase contained the 38 kd, 43 kd, and 68kd antigens according to the present invention as determined by immunoblotting as described in above. Three volumes of ethanol were added to the Triton extract at 4° C. to precipitate the proteins and wash away the Triton X-114.

The sample was then centrifuged at 10,000 × g for 10 minutes at 4° C. and the resulting pellet was dissolved in SDS containing sample buffer, and the resulting solution was loaded onto a 10% SDS-PAGE gel and electrophoresed. The proteins were then transferred from the SDS-PAGE gel onto activated GF/C filters (Whatman). The conditions for SDS-PAGE and electroblotting were essentially the same as described in J. Vandekerckhove et al., *Eur. J. Biochem.*, 152, 9–19 (1985) and Applied Biosystems User Bulletin No. 25, Nov. 18, 1986. The proteins on the electroblot were visualized by staining with a dipentyl-oxacarbocyanine iodide, and the 38 kd band was excised and was sequenced on an Applied Biosystems 470A sequencer. The following N-terminal sequence was determined: Thr-Ser-Asn-Thr-Gly-Val-Val-Lys-Gln-Glu-Asp-Val-Ser.

Following N-terminal sequence analysis, the 38 kd protein in the electroblots was treated with CNBr (10 µl of 0.1 g/ml) in 100 µl of 70% formic acid for 16 hours at room temperature to open new amino terminii following methionine residues for sequence analysis. The following sequence, wherein "X" denotes an unidentified amino acid and a "/" denotes an alternative identification for an amino acid, was obtained from the 38 kd blots after CNBr cleavage: X-X-X-Tyr/Leu-Phe-Val-Thr-Val/Asp/Asn-Glu-Ileu-Leu-Tyr-Asp-Val-Gly-Val-Phe.

EXAMPLE 2

N-Terminal Sequence Analysis of 43 kd Antigen

TX-114 ™ extraction was performed on 50 mg of *M. hyorhinis* protein harvested according to the procedure described in Example 1 above. The TX-114 ™ extract was made up to 10 ml in 20 mM ethanolamine, pH 9.0 and loaded onto a 1 ml column of DEAE-Sephacel equilibrated with the same buffer containing 0.5% Thesit ™ (Boehringer Mannheim GmBH, W. Germany) The proteins were eluted from the column using 20 mM sodium phosphate (pH 7.2) and 50 mM NaCl. The DEAE-Sephacel column was not used to enrich the antigens, but rather was primarily used to exchange the proteins from TX-114 ™ into Thesit ™. The eluted material from the above step was loaded onto 1 ml of heparin-agarose in a column (Sigma Chemical Company, St. Louis, Mo.) which was equilibrated with 20 mM sodium phosphate (pH 7.2) containing 50 mM NaCl.

The heparin-agarose flow-through contained 43 kd antigen, reduced levels of 38 kd antigens and several other proteins. A large portion of the 38 kd antigen was bound to the column and was eluted with 5 ml of 250 mM NaCl in 20 mM sodium phosphate (pH 7.2). The heparin-agarose flow-through was adjusted to 150 mM NaCl and loaded onto a 1 ml hydroxyapatite column (Bio-Rad Laboratories). The 43 kd antigen flows through and is mostly removed from contaminating bands around the same molecular weight. The 43 kd antigen which flowed through both of the above columns was concentrated to 150 μl using a YM10 filter (Centricon, obtained from Amcion Division, W. R. Grace and Company, Daneers, Mass.). The 43 kd antigen was electroblotted onto GF/C filters and the following N-terminal sequence, in which a "/" indicates an alternative identification for an amino acid, was obtained following the procedure as described in Example 1 above: Ser-Gly-Glu-Thr-Asp-Lys-Glu-Gly-Lys-Ile-Arg-Phe-Asp-Asn-Cys/Ser-Phe-Val-Lys-Asp.

EXAMPLE 3

Genomic Clone of the *M. hyorhinis* Gene Sequence Encoding the 38 kd Protein

From the amino acid sequence obtained from a CNBr-treated sample of gel-purified 38 kd protein, a mixed-sequence oligonucleotide probe (an 18 mer) was chemically synthesized according to the instructions of the inventors by Synthetic Genetics, San Diego, Calif. for: TAYGAYGTNGGNGTNTGG. All possible probes were constructed according to this sequence herein "Y" is a pyrimidine, "R" is a purine and "N" is any nucleotide residue. The last two G residues were incorrect and were predicted based upon an error in the amino acid sequence data.

Southern blotting experiments showed that this probe hybridized to a 3.4 kb HindIII fragment of *M. hyorhinis* DNA. Therefore, HindIII DNA fragments migrating at the 3.4 kb size range were electro-eluted from agarose gel and ligated to the plasmid vector, pUC19 [Biolabs, Beverly, Mass.] and used to transform *E. coli* cells to create a library of 3.4 kb *M. hyorhinis* DNA HindIII inserts. On screening the 3.4 kb HindIII-fragment library with the 18 mer probe, a clone, designated pM38-29/3, was isolated. It contained the 18 mer probe sequence identified by brackets in FIG. 1, but this clone was not complete. A 26 mer probe sequence identified by brackets in FIG. 1 was also used for screening. A more complete sequence was determined and is illustrated in FIG. 1.

In FIG. 1, it is believed that a complete amino acid sequence for a 38 kd RAA is provided in which residues indicated by an asterisk ("*") are hydrophilic, residues indicated by underlining are hydrophobic, and in which potential glycosylation sites (Asn-X-Ser/Thr) are overlined. Hydrophilicity /hydrophobicity data and glycosylation data may be used to construct immunogenic fragments and peptides and to construct hydropathicity analogs of the 38 kd polypeptide.

Figure 2B:
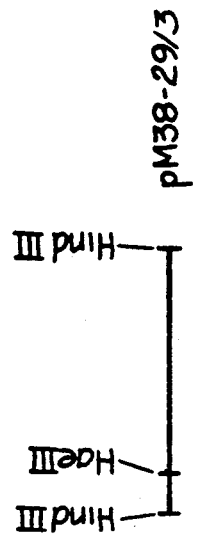
FIG. 2B is a restriction map of a clone designated pM38-29/3 which contains sequences encoding the C-terminal region of the 38 kd RAA.
Figure 2C:
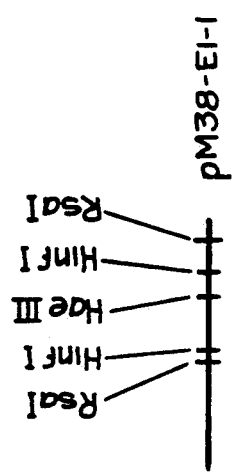
FIG. 2C is a restriction map of a clone designated pM38-E1-1 containing sequences encoding the N-terminal region of the 38 kd RAA and sequences 5' to the coding sequence; fragments in pM38-29/3 and pM38-E1-1 contain the homologous restriction sites found in the corresponding DNA segment indicated in FIG. 2A.

The nucleotide sequence of a 400 bp AluI fragment obtained from clone pM38-29/3 containing the 18 mer sequence was determined [according to the procedures of Sanger et al., *Proc. Nat'l. Acad. Sci.* (*USA*), 74, 5463 (1977)]. It was found that the triplet TGA, which may code for termination in *E. coli*, codes for trp in *M. hyorhinis*, as indicated by parentheses around "trp" residues in FIG. 1. The 400 bp AluI fragment was then used as a probe to screen a library generated by cloning 11 kb EcoRI DNA fragments of *M. hyorhinis* in pUC19 [Maniatis et al., Molecular Cloning, Cold Spring Harbor Laboratory, Cold Spring Harbor, N.Y. (1982)]. The 400 bp AluI probe hybridized to an 11 kb EcoRI fragment of *M. hyorhinis* DNA. A clone pM38-El-1 was isolated. The insert was found to contain a 4.4 kb insert with 6.6 kb of the above 11 kb *M. hyorhinis* DNA sequence being deleted. This clone contained sequences that hybridized to a mixed-sequence probe: AAYACNGGNGTNGTNAARCARGARGA, pre-dicted from the N-terminal amino acid sequence of the 38 kd protein. All possible probes were constructed for the oligonucleotide sequence indicated above wherein "Y" is a pyrimidine, "R" is a purine and "N" is any nucleotide base. In FIG. 2, the restriction map of this 4.4 kb insert is illustrated. The indicated restriction endonuclease cleavage sites indicated by small, vertical bars in FIG. 2 in the map of clone pM38 El-1 matched with corresponding sites which were those independently determined through restriction endonuclease analysis of *M. hyorhinis* DNA.

EXAMPLE 4

Genomic Clone of the *M. hyorhinis* Gene Sequence Encoding the 43 kd Protein

From the N-terminus amino acid sequence of the 43 kd protein (see Example 2) a 44 mer oligonucleotide with the following sequence was synthesized: GG(A/T) GAAAC(A/T)GATAAAGAAGG(A/T)AT(A/T)AGAAT(A/T)TTYGATAA. The choice of codons was made based on the codon usage in the gene encoding the 38 kd protein in mycoplasma. The oligonucleotide was then used to screen a size-selected partially-digested HindIII *M. hyorhinis* genomic library. The library was constructed by (i) first under-digesting *M. hyorhinis* DNA with HindIII, (ii) isolating DNA fragments of about 10kb using a sucrose gradient, and (iii) inserting the DNA fragments into the plasmid vector pUC19. Four clones were screened as positive with the oligonucleotide probe tire coding sequences for the 43 kd protein. The restriction map of the insert is shown in FIG. 4, and the map was verified by Southern blot analysis of genomic DNA.

Sequencing of the gene was carried out using standard technology (see Example 3) by both subcloning fragments into M13 and using the primer-directed method. The nucleotide sequence so determined is shown in FIG. 3. There are four TGA codons that appear to code for trp residues in *M. hyorhinis*.

EXAMPLE 5

Hybridomas Secreting IgM Antibodies Which May Be Specific For Regression-Associated Antigens Two adult female C3H mice were immunized with about 10.0 μg protein aliquots of A375 (ING A) membrane preparations determined to contain regression-associated antigens by immunoblotting as described above. The mice were immunized subcutaneously with membranes admixed with incomplete Freund's adjuvant (total volume 0.2 ml) on days 0, 14 and 21. Serum taken on day 35 revealed an antibody titer of 1:200 against regression associated antigens in the immunoblot assay described above using 375 (ING-A) membranes as the source of regression associated antigens. A375 (ING-A) cells were deposited on Feb. 12, 1987 as accession number CRL 9321 with the American Type Culture Collection, 12301 Parklawn Drive, Rockville, Md. 20852.

At approximately seven weeks after immunization commenced, the mice were sacrificed, their spleens were removed and splenocytes were fused to murine myeloma partner cells essentially as described in Kohler et al., supra. Approximately 70 to 80 hybridoma colonies were analyzed. The supernatant media from these colonies were screened for the presence antibodies reactive with A375 cells (ING-A) (10,000 cells per well of a microtiter plate) by an ELISA.

In an ELISA according to the present invention, cultures of A375 cells contaminated with *M. hyorhinis*, namely ING-A cells, or A375 cells which were free from *M. hyorhinis* were propagated in RPMI 1640 medium containing 10% fetal calf serum. When the cultures reached confluency, the medium was decanted, cells were rinsed twice with phosphate buffered saline PBS), and cells were removed by incubation with PBS containing 2.5 mM EDTA. The cells were pelleted by centrifugation and rinsed once with PBS followed by pelleting and resuspension in PBS at 10,000 cells per 50 µl.

Polyvinyl ELISA plates were prepared with unfixed cells by aliquoting the cell suspensions into 96 well plates using 50 µl per well. The plates were incubated at 37° C. overnight to allow for complete drying of the wells and effective attachment of cells to the bottoms of the wells.

The multiwell plates thus prepared were blocked with 5% nonfat milk in PBS. After washing with PBS, individual wells were incubated with 5 µl of hybridoma supernatant diluted with 45 µl of PBS for 3 hours at 37° C. Wells were then washed and incubated with a 1:350 dilution of peroxidase-congugated goat anti-mouse antibody (Sigma Chemical Company, St. Louis, Mo.) as recommended by the manufacturer. Plates were subsequently washed, incubated with orthophenylenediamine (Sigma Chemical Company) and color formation was terminated by adding 10 µl of 6 N HCl per well. ELISA plates were read at 492 mu and positive signals ranged from 0.7 to 1.3 with background signals of 0.1 to 0.2.

Only antibodies reactive (at a level of greater than 5 to 10 times background signal) with A375 (ING-A) cells, which contain RAAs, and non-reactive with RAA-negative cells were subjected to subcloning. Approximately six independent subclones were generated in this fashion. The subcloned hybridomas retained their specific reactivities for cells containing RAAs.

In addition, these subclones were screened by the above ELISA for reactivity with a partially-purified heparin-agarose column fraction (250 mM NaCl eluate as described in Example 2) of solubilized regression-associated antigens from *M. hyorhinis*. These subclones demonstrated some differences in the extent of reactivity with the partially-purified regression associated antigen protein (½ µg/well). Most had positive titers (3 to 5 times background signals). The clones were designated 3C3, 2H8, 2C8, 3G2, and 2H7. The clone designated 3C3 was deposited on September 16, 1987, under the accession number ATCC HB 9540, with the American Type Culture Collection, 12301 Parklawn Drive, Rockville, Md. 20852.

Typing of these hybridomas (determined using an isotyping kit and procedure available from HyClone Laboratories, Inc., Logan, Utah) revealed them to be secreting IgM antibodies. Preliminary indirect immunoperoxidase or immunofluoresence screening [according to the procedure described in Sheehan et al., *Theory and Practice of Histotechnoloqy*, eds. C. V. Masby, Co., 310-326 (1980)] on fresh frozen human tumors has shown a monoclonal secreted by the subclone designated 3C3 to be 3+to 4+(positive) on two independently-derived Ewing's sarcomas, a mesothelioma, a breast carcinoma metastatic to spleen, lung and liver, and weakly reactive (1+) with a breast adenocarcinoma. This antibody was non-reactive with a biliary carcinoma. Against human tumor cell lines, 3C3-secreted monoclonal antibody reacts strongly with Ewing's sarcoma and mesothelioma cell lines derived from the above tumors as well as osteosarcoma, colon carcinoma, adenocarcinoma of the lung, spindle cell sarcoma, bladder carcinoma and breast carcinoma cell cultures established by enzymatic disruption of minced fresh tumor biopsies followed by plating in RPMI 1640 medium containing between 10% to 20% fetal calf serum. It also reacts with an established tumor cell line designated M14 derived from a human melanoma tumor [Moy et al., *J. Surg. Oncol.*, 29, 112–117 (1985)]. It is non-reactive with two other melanoma cell lines, with human fibroblastic cells in culture and against a panel of frozen sections of normal human tissues (excluding endothelial and myofibroblastic cells) obtained from autopsy of a sin9le patient including esophogous, liver, stomach, skeletal muscle, thyroid, urinary bladder, spleen, pancreas, lung and cerebellum. Certain reactivity of the 3C3 monoclonal antibody has been observed with some human endothelial cells and myofibroblasts in immunohistochemical staining studies using frozen sections of certain tissues.

EXAMPLE 6

Monospecific Polyclonal Antibodies Reactive With Purified 38 kd and 43 kd Antigens Polyclonal rabbit sera were generated by immunizing rabbits with the 38 kd RAA protein prepared essentially according to the procedure of Example 1 and isolated from polyacrylamide SDS gels and with the 43 kd RAA protein of Example 2.

Anti-38 kd antibodies were generated by immunization of two rabbits with the protein species migrating at 38 kd in gel slices of preparative SDS-PAGE. The *M. hyorhinis* protein used for SDS-PAGE was the heparin-agarose bound material (250 mM NaCl eluant) of Example 1. In Western immunoblot analysis, the anti-38 kd antibody, when used at 1:1000 dilution, recognized the 38 kd antigen in SDS-extracts of *M. hyorhinis* and other antigens of molecular masses ranging from 36.5 kd to 95 kd in SDS-extracts of several human tumor cell lines and fresh tumor extracts (Table 1). Indirect immunoperoxidase staining with anti-38 kd antibodies revealed positive reactivity to several human primary tumor cell cultures (mesothelioma, osteosarcoma and Ewing's sarcoma) as well as to frozen sections from human mesothelioma and breast carcinoma and also to an M14 human melanoma cell line [Moy et al., supra].

Anti-43 kd antibodies were generated by immunization of two rabbits with 43 kd gel slices from SDS-PAGE of the heparin-agarose flow-through material of Example 2. In Western immunoblot analysis, this anti-43 kd antibody, when used at 1:200 dilution, recognized 43 kd as well as 38 kd antigens in SDS extracts of *M. hyorhinis.*

Cell cultures identified in Table 1 are cultures derived from primary culutres of the respective human tumors as described in Example 5 or are identified as "ATCC" and are obtained as human tumor cell lines from the American Type Culture Collection (Rockville, Md.).

TABLE 1

ImmunoReactivity of Anti-38 kd Sera

| Cell/Tumor Extracts | Protein Bands Detected |
| --- | --- |
| Normal colon tissue extract | (faint) 36.5 kd |
| Osteosarcoma cell culture | (strong) 55 kd |
| Melanoma cell line (M14) | (faint) 55 kd, 68 kd |
| Ovarian carcinoma cell culture | (strong) 43 kd, (weak) 60 kd |
| Metastic colon cancer carcinoma extract | (strong) 55 kd |
| Ovarian carcinoma cell culture | (none) |
| Breast carcinoma extract | (faint) 48 kd, (faint) 95 kd |
| Lymphoma cell | (strong) 43 kd, (strong) 60 kd |
| Normal fibroblast (GIN-1)/ATCC | (strong) 55 kd |
| Colon carcinoma cells (SW4/80)/ATCC | (moderate) 60 kd |
| Colon carcinoma cells (LOVO)/ATCC | (moderate) 60 kd |
| Lung carcinoma cells (A549)/ATCC | (strong) 58 kd, (weak) 60 kd |

EXAMPLE 7

Nucleic Acid Probes for RAA Gene Sequences

Deoxyribonucleic acid hybridization probes may be synthesized using sequences as illustrated in FIG. 1 or of FIG. 3 by the procedure of Caruthers. U.S. Pat. No. 4,415,732 and ribonucleic acid probes may be made by in vitro transcription from them. Hybridization conditions according to the present invention may generally be defined as reactions functionally equivalent to hybridization carried out in 4×SSC and 0.5% SDS at a termperature of 65° C. in the last wash.

Plasmids including DNA sequences according to the present invention may be labeled with a radioactive isotope. [Rigby et al., *Mol. Biol.*, 113, 237–251 (1977) or Feinberg et al., *Anal. Biochem.*, 132, 6–13 (1983)] or with a non-radioactive chemical tag [Leary et al., *Proc. Natl. Acad. Sci. (USA)*, 80, 4045–4049 (1983)] and used as probes. Such plasmids may also be used to synthesize labeled RNA probes [Melton et al., *Nucleic Acids Res.*, 2, 7035–7055 (1984)]. The labeled probes may be used to detect the presence of homologous DNA sequences and/or mRNA sequences encoded by these DNA sequences in tumor cells either by the Southern or Northern hybridization procedure [Southern et al., *J. Mol. Biol.* 98, 503 (1975); Thomas, *Proc. Natl. Acad. Sci. (USA)*, 77, 5201–5205 (1980)] or by dot blot or slot blot hybridization [Kafatos et al., *Mol. Cell. Biol.*, 3, 1097–1107 (1983)], or by in situ hybridization techniques [Brahic et al., *Proc. Natl. Acad. Sci. (USA)*, 75, 6125–6129 (1978)].

One type of hybridization assay which may be performed using the hybridization probes according to the present invention is called solution hybridization. In this procedure, a labeled probe nucleic acid is added to a solution of a sample to be searched for a target nucleic acid. In order to ensure that both the probe and a target are in a single-stranded state suitable for hybridization, the sample and probe are heated in order to break (denature) the hydrogen bonds which are found between complementary strands of a double-stranded probe or a double-stranded target, or which are found within secondary structure of a probe or target. Upon cooling, the reaction is reversed and double-stranded nucleic acid is allowed to form. The amount of double-stranded nucleic acid which forms may be determined by scintillation counting of the label on the probe after degradation of unhybridized single strands or after isolating double-stranded DNA by passing the hybridization solution over a hydroxyapatite column which selectively retains the double-stranded form.

In another type of hybridization assay to which the probes according to the present invention may be applied, denatured target nucleic acid is immobilized on a support. Retention of a labeled probe on a support-bound target after passage of the support-bound target through a solution containing the probe permits detection and quantitation of the target by measurement of the amount of bound label. See, e.g., Falkow et al., U.S. Pat. No. 4,358,535; and Shafritz, European Patent Application Publication No. 62286.

Yet another type of hybridization assay of the present invention in which the probes accordingly may be employed is called a "sandwich" hybridization. A two-step sandwich hybridization procedure involves the use of an immobilized target nucleic acid which is exposed in a first step to a first nucleic acid probe having a first portion complementary to the target and having a second portion which is not complementary to the target. In a second step, a second, labeled nucleic acid probe, which is complementary to the second portion of the first probe, is allowed to hybridize to the first probe, forming a "sandwich" comprising the first probe between the target and the second probe. Dunn et al., *Cell*, 12, 23–36 (1977).

A one-step sandwich assay may also be performed. This type of assay involves the use of a first nucleic acid probe immobilized on a filter. The first nucleic acid probe immobilized on a filter. The first nucleic acid probe is complementary to a first portion of a target nucleic acid. In a single step the filter-bound first probe is exposed to a sample to be searched for the target nucleic acid sequence and to a second, labeled nucleic acid probe complementary to a second portion of the target nucleic acid which portion is separate from (i.e., non-overlapping with) the portion of the target to which the first probe is complementary. Ranki et al., U.S. Pat. No. 4,486,539.

Another approach to hybridization, called blot hybridization involves separating sample nucleic acids according to size by electrophoresis through a gel and then transferring them to a nitrocellulose filter on which they are immobilized in their relative positions on the gel. Because any target in the sample is confined to a distinct band on the filter, even weak signals resulting from small amounts of target may be distinguished from non-specific background after exposure to a radiolabeled probe. Bornkamm et al., *Curr. Top. Microbiol. Immunol.*, 104, 288–298 (1983).

Where a sample is in the form of a touch smear of a fluid, a section through cells, or chromosomal squashes from cells on slides, hybridization may be performed in situ.

Generally, a radioactively labeled probe according to the present invention is applied to the sample which is bound to the slide in a histological preparation. After coating the slide with a photographic emulsion, autoradiographic procedures reveal the location of target-probe hybrids by means of clusters of silver grains formed in the emulsion over the hybridization site.

EXAMPLE 8

Synthetic Peptide Antigens/Immunogens Related to RAA Sequences

The DNA sequences as illustrated in FIG. 1 and FIG. 3 have been used as shown therein to deduce the corresponding protein sequence. Peptides corresponding to different portions of RAA proteins, preferably 12-20 amino acid residues in length, may be chemically synthesized by solid-phase methods [Marglin et al., *Ann. Rev. Biochem*, 39, 841-866 (1970)]. Such peptides may then be used to elicit specific polyclonal and monoclonal antibodies [Lerner, Nature, 299, 592-596 (1982); Niman et al., *Proc. Nat'l. Acad. Sci. (USA)*, 80, 4949-4953 (1983)]. The DNA sequences provided in FIG. 1 and in FIG. 3 facilitate the design of immunogenic 25 peptides corresponding to different regions of the 38 kd and 43 kd RAA proteins, suitable immunogenetic regions of which may be determined according to procedure known to those skilled in the art [Novotny et al., *Proc. Natl. Acad Sci. (USA)*, 83, 226-230 (1986) and Van Regenmortel, *Trends Biochem. Sci.*, 11, 36-39 (1986)].

EXAMPLE 9

Production of RAA Antigens or Fragments Thereof Using Recombinant DNA Technology Complete and partial RAA gene products may be expressed in bacteria, yeast or mammalian expression systems by inserting a DNA sequence as illustrated in FIG. 1 or of FIG. 3 into plasmid, phage or viral expression vectors [Vieira et al., *Gene*, 19, 259-268 (1982); Young et al., *Proc. Nat'l. Acad. Sci. (USA)*, 80, 1194-1198 (1983); Bitter et al., *Gene*, 32, 263-274 (1984); Cepko et al., *Cell*, 37, 1053-1062 (1984); and Gorman et al., *Mol. Cell. Biol.*, 2, 1044-1051 (1982)]. Alternatively, *M. hyorhinis* may be cultured, e.g. as in Example 1, and RAAs may be isolated and purified therefrom, e.g., as in Example 1. The expressed proteins may be purified and used in immunotherapy or to raise specific antibodies.

In addition to the ELISA and immunoblot assays described herein, polyclonal and monoclonal antibodies according to the present invention may be used separately or in combination with purified and isolated RAAs according to the present invention in any suitable immunoassay.

Target antigens may be adsorbed to polyvinyl titration plates and various dilutions of polyclonal or monoclonal RAAs may be applied to the individual wells in a radioimmunoassay [Tsu et al., *Selected Methods in Cellular Immunology*, Mishell et al., eds., Freeman Publishing Company, San Francisco, 373-397 (1980)].

In addition, it is contemplated that immunoassays as described herein may be varied as is clear to one skilled in the art. Such variations include the use of monoclonal and polyspecific antibodies in conventional and sandwich ELISA [Kemeny et al., *J. Immunol., Methods*, 87, 45-50 (1986)].

EXAMPLE 10

Uses of RAAbs

Tumor localization and therapy may be performed employing RAAbs according to the present invention by generally following radiolabeling and scanning procedures set forth in and referenced in Goldenberg, U.S. Pat. No. 4,348,376, and Goldenberg, U.S. Pat. No. 4,444,744. It is also contemplated that fragements of RAAbs and hybrid chimeric antibodies and fragments of RAAbs are useful for scanning and therapy as well; [Goldenberg, U.S. Pat. No. 4,331,647; Stevenson et al., *Bioscience Reports*, 5, 991-998 (1985)].

Conjugation of RAAbs with immunotoxins may also be employed in therapy. [Blakey et al., *BioEssays*, 4, 292-297 (198 )].

EXAMPLE 11

Construction of an Intracellular 38 kd RAA Expression Vector

Figure 5A:
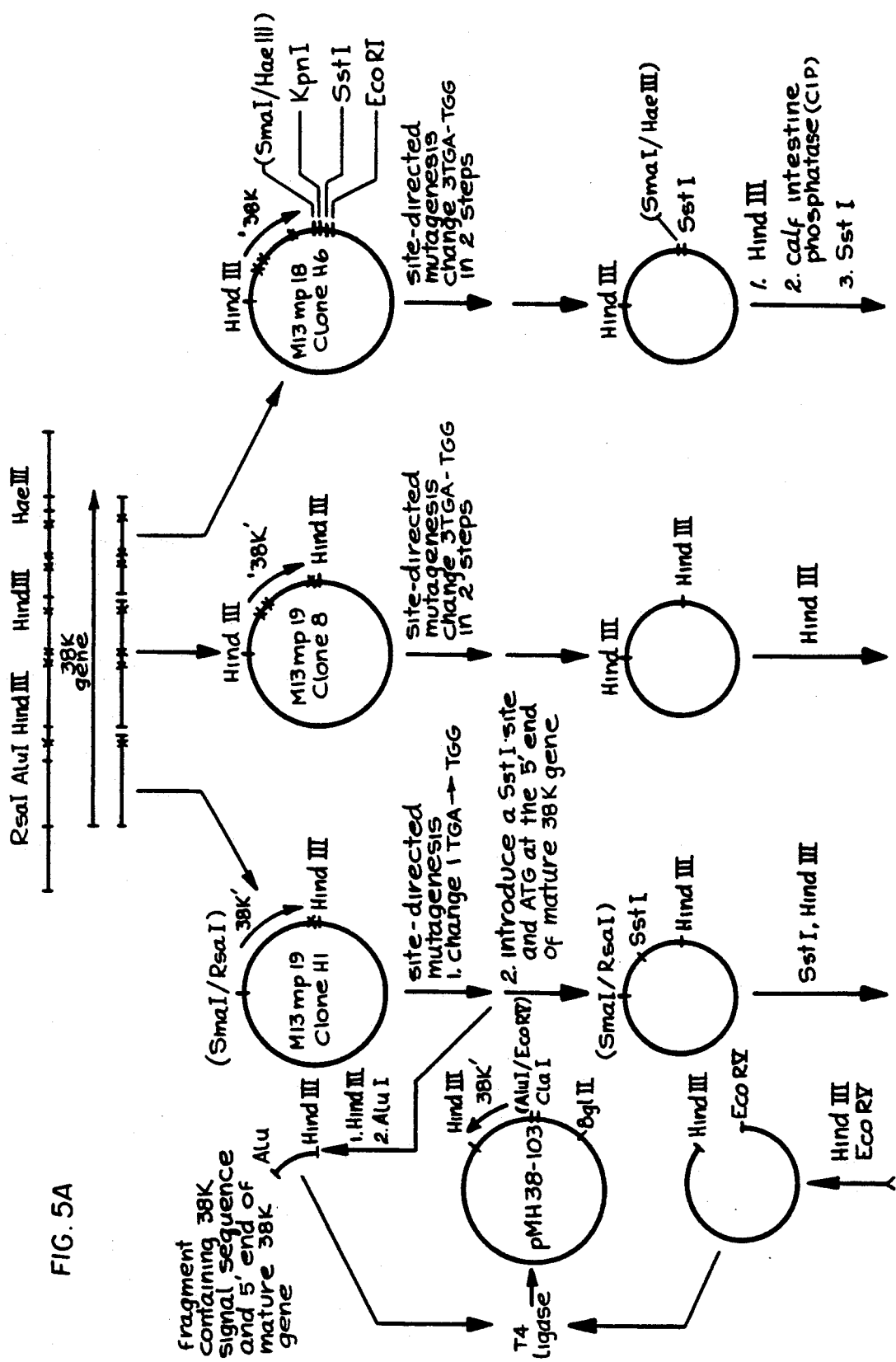
FIG. 5 is a schematic depiction of a procedure for construction of an expression vector for a 55 kd fusion RAA protein, according to the present invention.
Figure 5B:
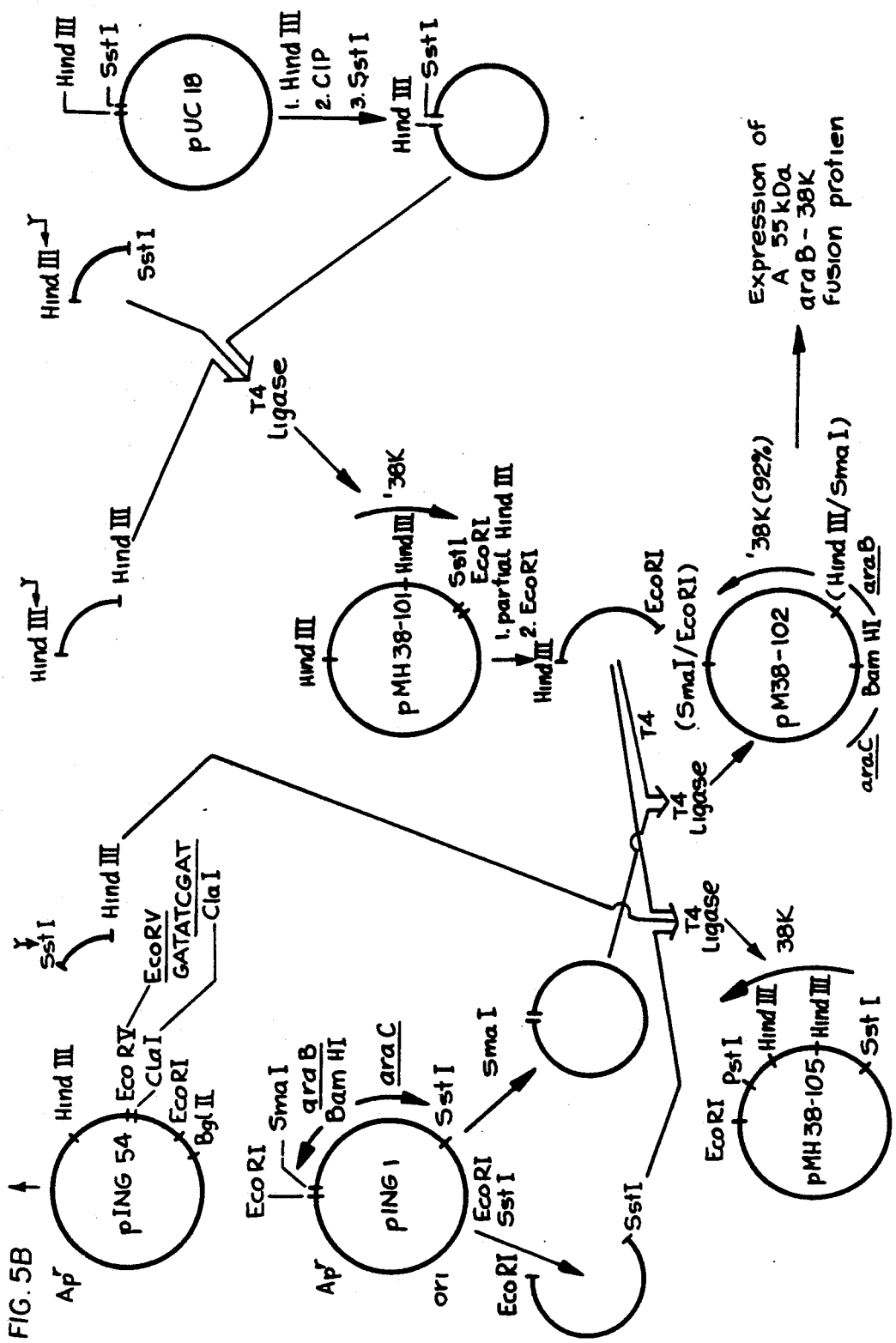

As illustrated in FIG. 5, an expression vector for a 55 kd araB 133 kd RAA fusion protein was constructed according to the following procedures. A *M. hyorhinis* gene encoding the 38 kd regressen protein was split into three fragments (450 bp RsaI/HindIII, 543 bp HindIII/HindIII, and 630 bp HindIII/HaeIII) which were inserted into SmaI/HindIII and HindIII digested M13mp19 (New England Biolabs, Beverly, Mass.), and HindIII/SmaI digested M13mp18 (New England Biolabs, Beverly, Mass.) phage vectors, respectively.

Using synthetic oligonucleotides as mutagenesis primers, site-directed mutagenesis was performed [Kramer et al, *Nucleic Acids Res.*, 12, 9441 (1984)] on: M13mp19 containing the RsaI/HindIII fragment (Clone H1) to change one TGA codon to TGG codon and insert an SstI site and an ATG codon into the 5'-end of the mature 38 kd gene; on M13mp19 containing the HindIII/HindIII fragment (Clone 8) to change three TGA codons to TGG codons; and on M13mp18 containing the HindIII/HaeIII fragment (Clone H6) to change three TGA codons to TGG codons.

The HindIII gene fragment was then removed from the mutagenized clone 8 by HindIII digestion. A HindIII/SstI fragment, which included the HindIII/HaeIII gene fragment, was removed from mutagenized clone H6 by HindIII digestion, calf intestine phosphatase ("CIP") treatment to remove the 5'-end phosphate, and then SstI digestion. These two fragments were ligated together, using T4 ligase, into the HindIII digested, CIP treated and SstI digested pUC18 (Pharmacia, Piscataway, N.J.). The CIP treatment prevents the two-piece ligation without the HindIII/HindIII fragment. The resulting intermediate product, pMH38-101, contains 92% of the 38 kd gene (i.e., all of the gene except a portion of the 5' end). As a matter of course, after every ligation step in this and the following examples the resulting plasmids were amplified by transformation into *E. coli* strain MC1061 and replication, and the presence of the appropriate insert in the plasmids was confirmed by restriction enzyme digestion and gel electrophoresis. In addition, plasmid pMH38-101 was also checked for the correct orientation of the HindIII/HindIII fragment. Generally in this and the following examples, cells transformed with the appropriate plasmid were selected on the basis of amplicillin resistance thereof, except for pIT2 with which tetracycline resistance was employed.

Plasmid pMH38-101 contains an EcoRI recognition site adjacent to the SstI site at the 3'-end of the 38 kd gene. By partial HindIII and EcoRI digestions, followed by gel electrophoresis to separate fragments with different sizes, the 1170 bp HindIII/EcoRI fragment was purified. This fragment included both of the previously mentioned HindIII and HindIII/HaeIII fragments of gene. The HindIII/EcoRI fragment was blunt-ended by T4 polymerase treatment, then inserted, using T4 ligase, into a SmaI-digested expression vector, pING1 [constructed from pMH6 (ATCC#39450) as described in Johnston et al., *Gene,* 34,137–145 (1985) and also in Lai et al., PCT Publication No. WO 86/04356]. Plasmid pING1 contains the araB promoter and the araC regulatory gene. The ligation product, pMH38-102, expressed a 55 kd fusion protein consisting of a partial araB gene and 92% of the 38 kd gene, when transformed into *E. coli* strain MC1061 and indiced with L-arabinose.

The 5'-end portion of the 38 kd gene was separated from the mutagenized Clone H1 by digestion with SstI and HindIII. This SstI/HindIII fragment was mixed together with the 1170 bp HindIII/EcoRI fragment containing the other 92% of the gene, then ligated into EcoRI- and SstI-cut pING1. This product, pMH38-105, contains the completed gene coding for the 38 kd regressen protein.

Figure 6A:
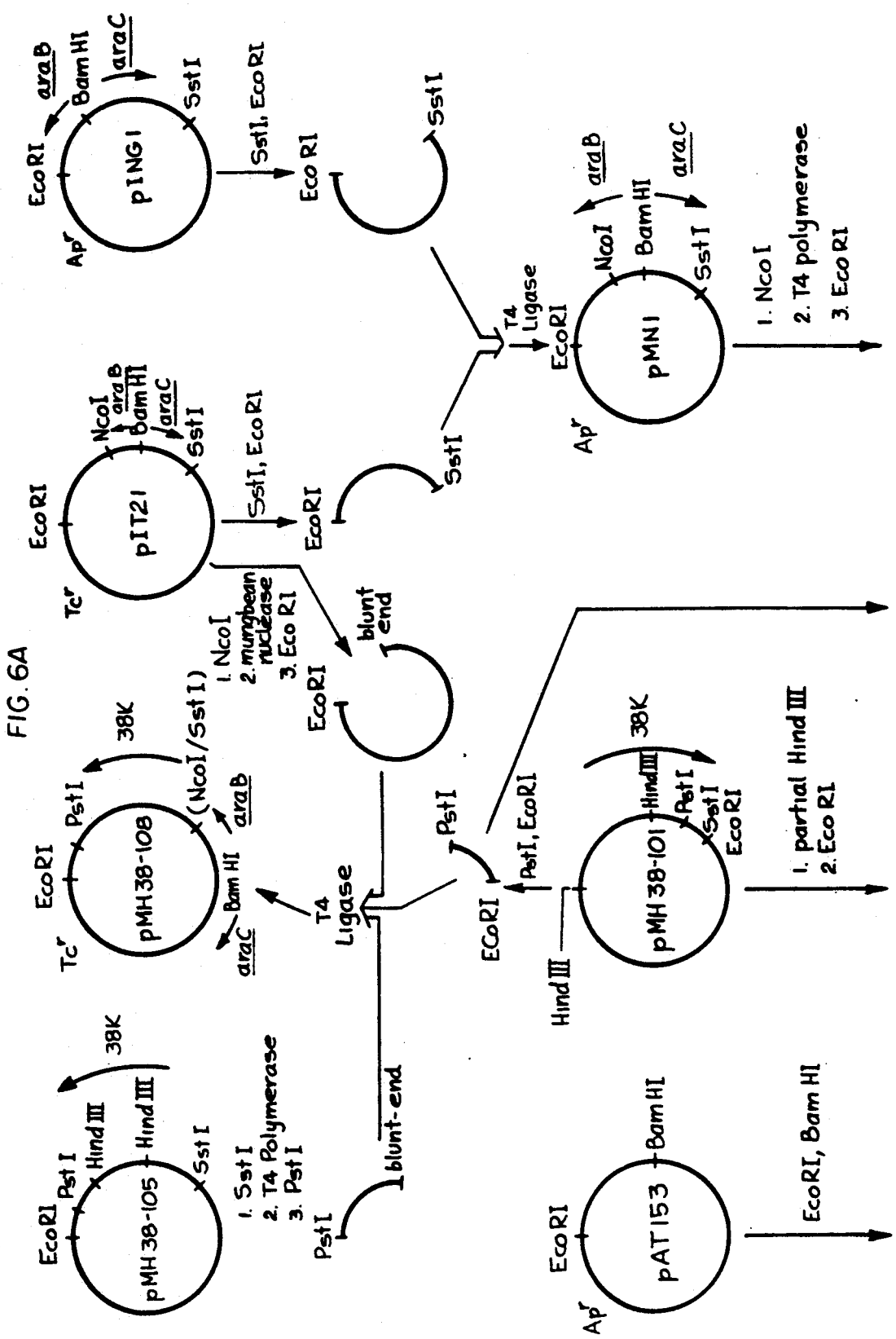
FIG. 6 is a schematic depiction of a procedure for construction of an expression vector for a 38 kd secreted RAA protein, according to the present invention.
Figure 6B:
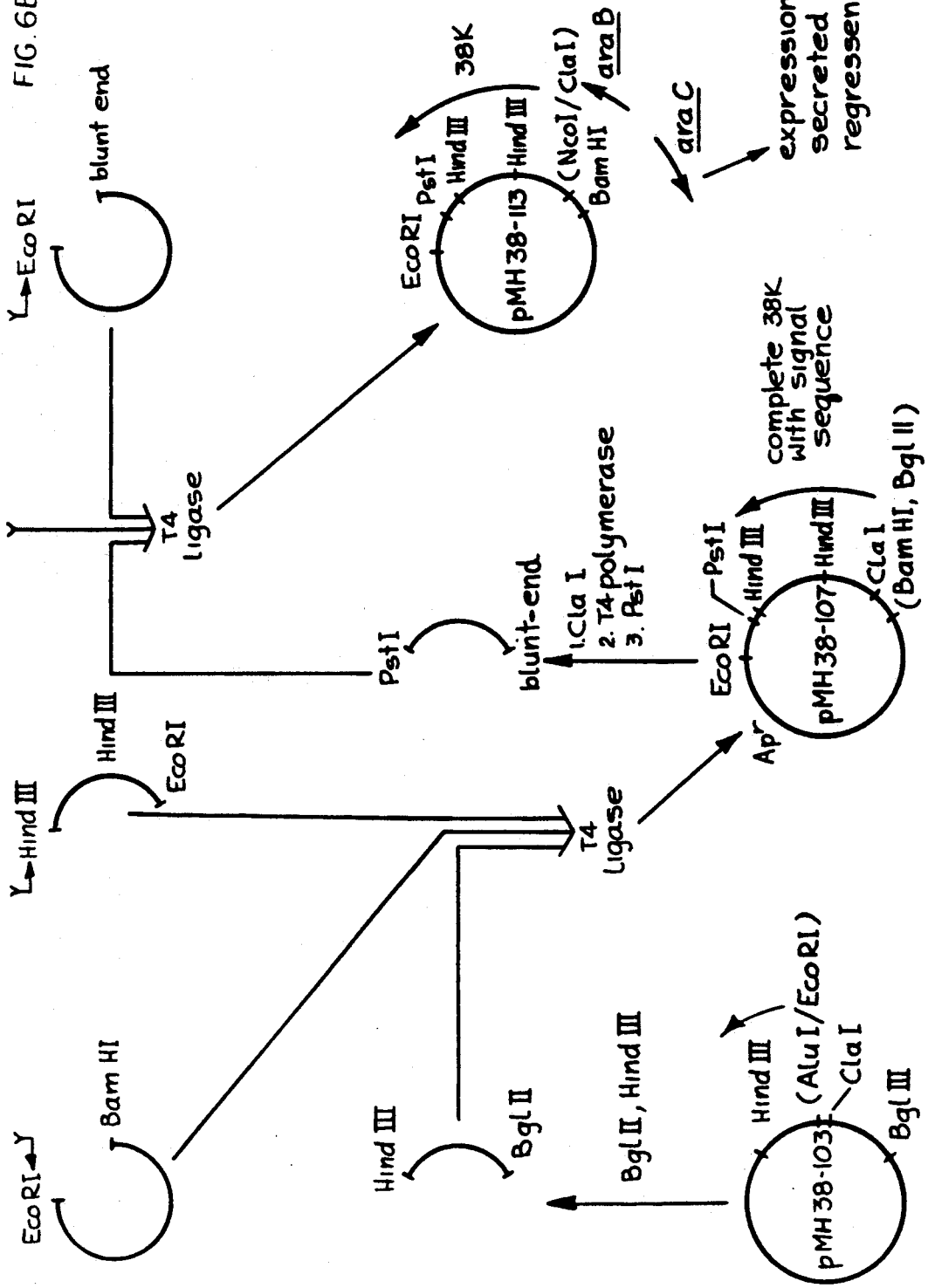

As illustrated in FIG. 6, within the intermediate plasmid pMH38-105, the 3'end of the 38 kd gene was characterized by a PstI recognition site . followed by an EcoRI site. The plasmid was digested with SstI, blunt-ended with T4 polymerase, then digested with PstI to yield an 800 bp blunt-end/PstI fragment. The missing 455 bp EcoRI/PstI fragment (at the 3' end of the gene) was obtained from EcoRI and PstI digestion of pMH38-101. Plasmid pIT2 [constructed from pING1 as described in Masson et al., *Nucleic Acids Res.,* 14, 5693–5711 (1986)] was cut with NcoI, its "sticky-end" was cleaved off with mung bean nuclease, and then it was cut with EcoRI. The digestion product was then ligated together with the EcoRI/PstI and PstI/blunt end fragments, using T4 ligase. The resulting intermediate plasmid, pMH38-108, contains the completed 38 kd gene linked to the araB promoter and ribosome binding site.

Figure 7:
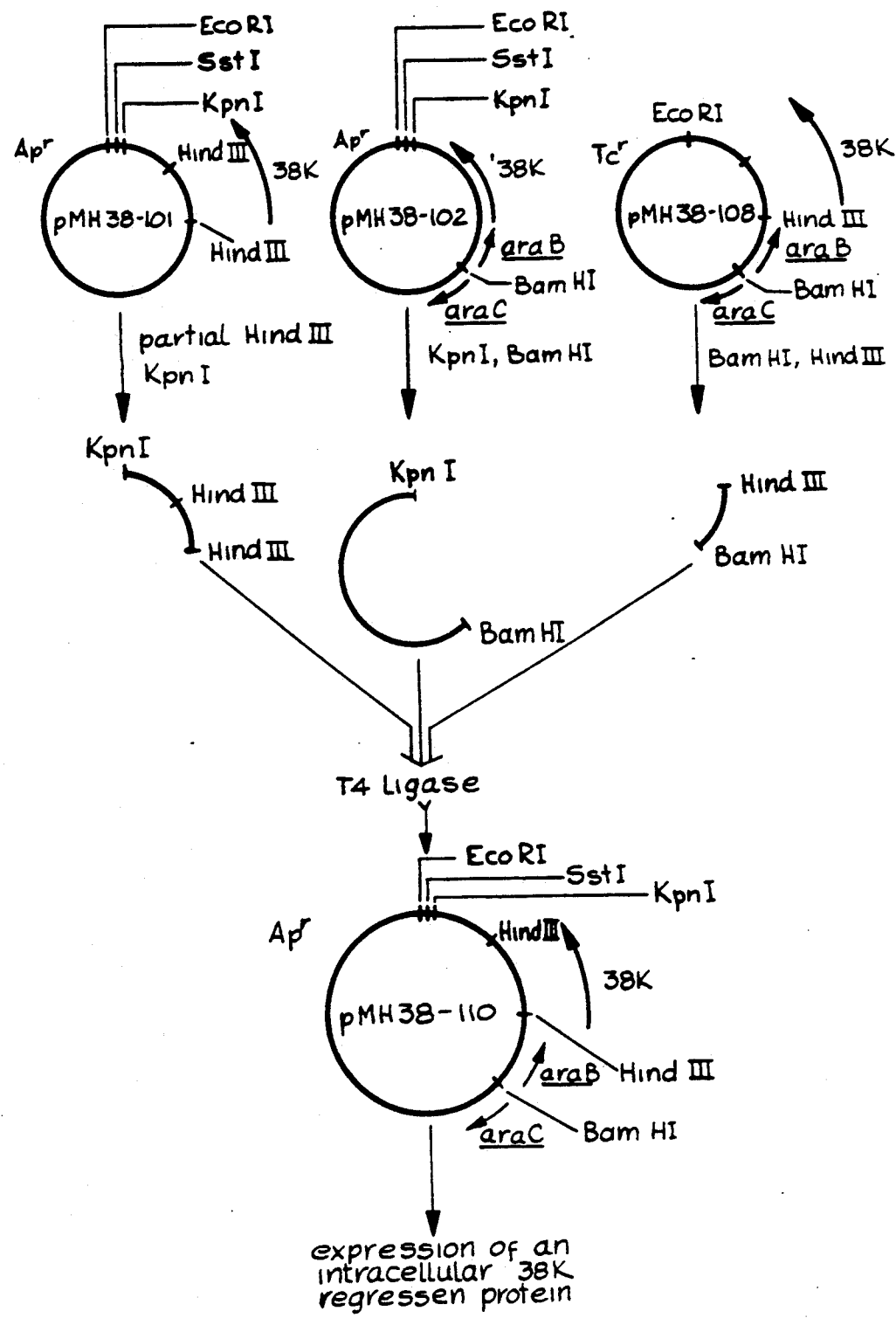
FIG. 7 is a schematic depiction of a procedure for construction of an expression vector for a 38 kd intracellular RAA protein, according to the present invention.

As illustrated in FIG. 7, both intermediate plasmids pMH38-101 and pMH38-102 were characterized by a KpnI recognition site immediately preceding the EcoRI site. A 1170 bp KpnI/HindIII fragment containing the 3'-end portion of the 38 kd gene was obtained from pMH38-101 by partial HindIII and KpnI digestion followed by gel electrophoresis. A HindIII and BamHI digestion was performed on pMH38-108, yielding a HindIII/BamHI fragment that contained the fusion of the araB promoter and the 5'-end portion of the 38 kd gene. Using T4 ligase, this HindIII/BamHI fragment was ligated, together with the 1170 bp KpnI/HindIII fragment of the gene, into pMH38-102 that had been digested with BamHI and KpnI. The resulting product, pMH38-110, expressed an intracellular 38 kd regression protein upon transformation into *E. coli* strain MC1061 and induction with L-arabinose. Plasmid pMH38-110 in *E. coli* MC1061 was deposited on Sep. 15, 1988 under accession number ATCC 67799 with the American Type Culture Collection, 12301 Parklawn Drive, Rockville, Md. 20852.

EXAMPLE 12

Construction of a Secreted 38 kd RAA Vector

As illustrated in FIG. 5, after the first site-directed mutagenesis to change a TGA codon to TGG codon, an AluI/HindIII fragment containing the 38 kd gene signal sequence along with the 5'-end of the mature 38 kd gene was isolated from clone H1. This small fragment was inserted, using T4 ligase, into plasmid pING54 [construction described in Weickmann et al., European Patent Publication No. 255823 in Example 5 thereof], which had been digested with HindIII and EcoRV, to form an intermediate, pMH38-103. The purpose of this construction was to adjust the reading frame of the 38 kd gene for the subsequent cloning using the adjacent ClaI site (ATCGATATC).

As illustrated in FIG. 6, plasmid pMH38-103 was characterized by a BglII site followed by a ClaI site, followed by the EcoRV/AluI junction where the fragment was inserted. This plasmid was digested with BglII and HindIII, forming a BglII/HindIII fragment. The small 320 bp BglII/HindIII fragment from pMH38-103 and the 1170 bp HindIII/EcoRI fragment (purified as described in the previous example), which contained the majority of the 38 kd gene (excluding the 5'-end), were ligated into pAT153 (Amersham, Arlington Heights, Ill.) that had been cut with EcoRI and BamHI which generate a sticky and compatible with the end generated by BglII. The resulting intermediate was called pMH38-107.

The plasmid pMH38-107, like its relatives pMH38-101 and pMH38-105, also contains a PstI site near the 3'-end of the 38 kd gene and near the EcoRI site outside the gene. This plasmid was digested with ClaI, treated with T4 polymerase to fill in the 5' cohesive end, and then digested with PstI. This 880 bp PstI/blunt-end fragment, together with the 455 bp PstI/EcoRI fragment from pMH38-101, were ligated into plasmid pMN1 which had been digested with NcoI, filled-in with T4 polymerase, then digested with EcoRI. The resulting product, pMH38-113 secreted a 38 kd regressen protein upon transformation into *E. coli* strain MC1061 and induction with L-arabinose. Plasmid pMH38-113 was deposited in *E. coli* MC1061 on Sep. 15, 1988 under accession number ATCC 67801 with the American Type Culture Collection, 12301 Parklawn Drive, Rockville, Md. 20852. The plasmid pMN1 was constructed by digesting plasmids pIT2 and pING1 with EcoRI and SstI, then ligating the complementary portions with T4 ligase.

EXAMPLE 13

Construction of an Intracellular 43 kd RAA Vector

Figure 8A:
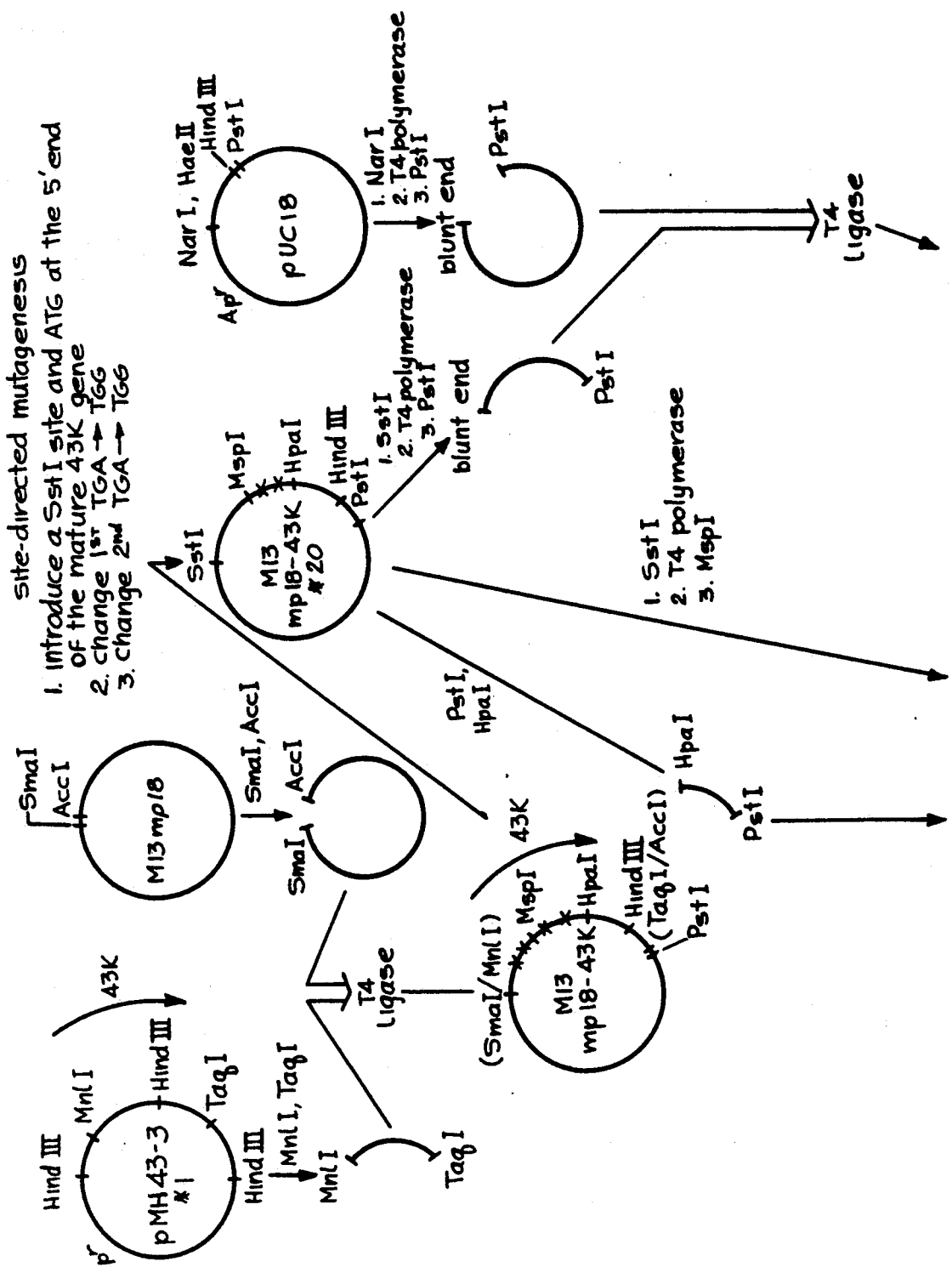
FIG. 8 is a schematic depiction of a procedure for construction of an expression vector for a 43 kd intracellular RAA protein according to the present invention.
Figure 8B:
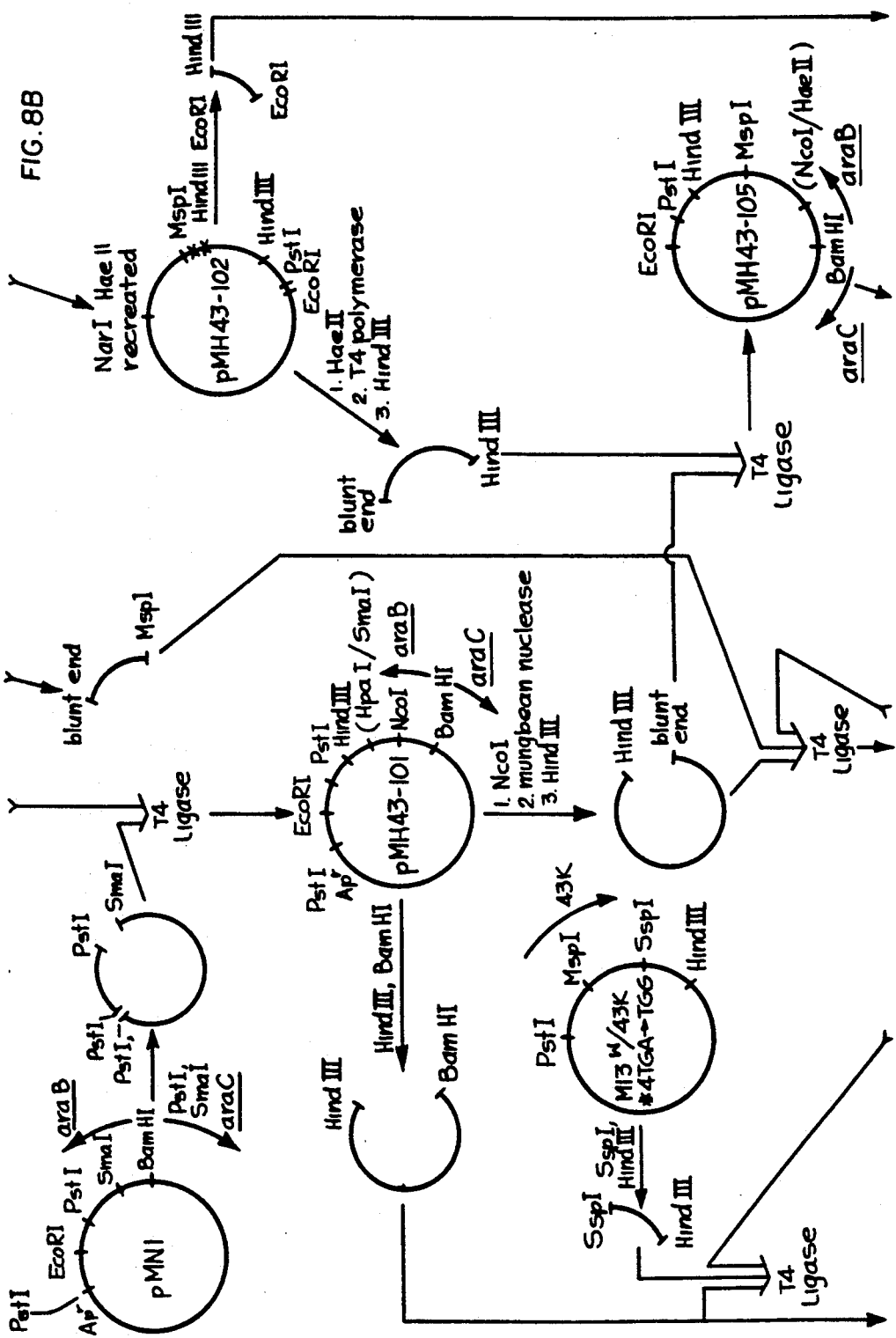
Figure 8C:
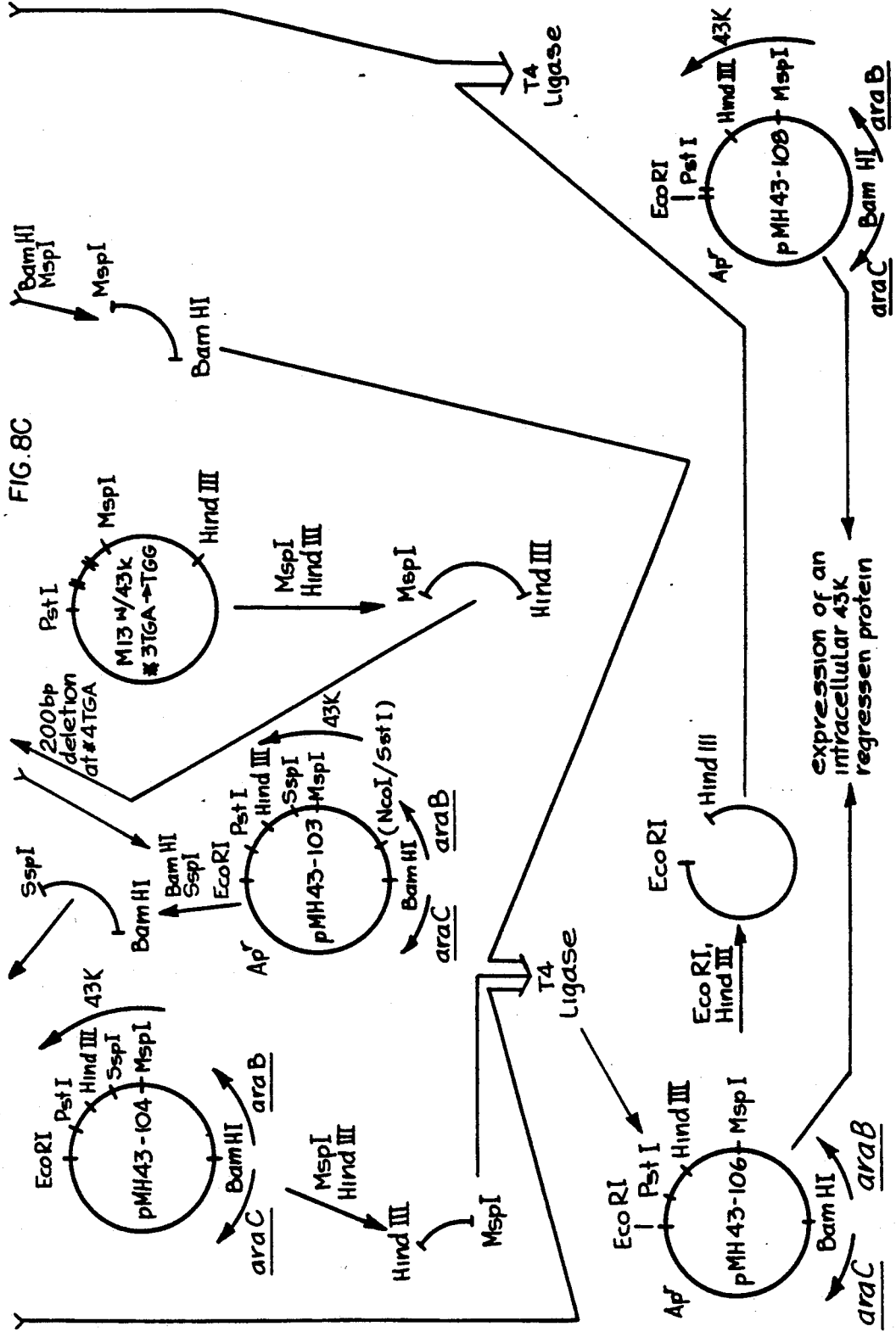

As illustrated in FIG. 8, pMH43-3 (one of the four clones the isolation of which is described in Example 4) was digested with MnlI and TaqI, to form a MnlI/TaqI fragment that contained the complete gene coding for the 43 kd regressen protein. This fragment was inserted into an M13mp18 phage vector that had been cut with SmaI and AccI, with T4 ligase, forming an intermediate called M13mp18-43 kd.

M13mp18-43 kd was then altered by site-directed mutagenesis [Kramer et al., *Nucleic Acids Res.,* 12, 9441–9456 (1984)]. A SstI site was introduced at the 5' end of the mature 43 kd gene, and the first two (out of a total of four) TGA codons were changed to TGG codons. The resulting vector was called M13mp18-43 kd-#20.

A blunt end/PstI fragment containing the complete 43 kd gene was obtained from the vector M13mp18-43K-#20, by digesting it with SstI, followed by blunt-ending with T4 polymerase, then digestion with PstI. This fragment was inserted, using T4 ligase, into a pUC18 plasmid (Pharmacia, Piscataway, N.J.) that had been cut with NarI, filled in with T4 polymerase, and PstI digested. The resulting intermediate, pMH43-102, contained the recreated NarI(HaeII) recognition site. As a matter of course, after every ligation step the resulting vectors were amplified by transformation into *E. coli* strain MC1061 and replication, and the presence of the appropriate insert was checked by restriction enzyme digestion and gel electrophoresis.

The 3' end of the 43 kd gene in the vector M13mp18-43K-#20 was characterized by a HindIII site followed by a TaqI/AccI site, followed by a PstI site. This vector was digested with PstI and HpaI, to form a small PstI/HpaI fragment that contained the 3' end of the 43 kd gene. Plasmid pMNl was cut with PstI and SmaI; the long PstI/SmaI fragment that contained the majority of the plasmid together with the small PstI fragment from pMNl were ligated with the PstI/HpaI fragment from M13mp18-43K-#20, using T4 ligase. The plasmid that contained both the longer PstI/SmaI and PstI fragments was selected for with marker bla. This intermediate was called pMH43-101.

The plasmid pMH43-101 was digested with NcoI, followed by treatment with mung bean nuclease to cleave off the cohesive end, and then digested with HindIII; this formed a large HindIII/blunt end fragment. Another, smaller blunt end/HindIII fragment was obtained by digesting pMH43-102 with HaeII, blunt-ending with T4 polymerase, and then digesting with HindIII. The two blunt end/HindIII fragments from pMH43-101 and pMH43-102 were ligated together with T4 ligase to form the intermediate pMH43-105. Plasmid pMH43-105 is characterized by a 7 bp segment between the araB ribosome binding site and the ATG codon of the 43 kd gene, and it still contains two TGA codons (#3 and #4) in the 43 kd regressen gene.

The vector M13-w/43K was constructed by ligating the HindIII fragment which contains part of the 43 kd gene to M13mp19 cut with HindIII. Site-directed mutagenesis [Kramer et al., *Nucleic Acids Res.*, 12, 9441–9456 (1984)] was used to change the third TGA codon to a TGG codon, which generated M13-w/43K-#3TGA->TGG (a spontaneous 200bp deletion was found in this clone which deleted out the region including the fourth TGA codon). Site-directed mutagenesis was also used to change the fourth TGA codon to a TGG codon, and generated M13-w/43K-#4TGA->TGG.

The vector M13mp18-43K-#20 was digested with SstI, blunt-ended with T4 polymerase, then digested with MspI, to yield a blunt-end/MspI fragment. This blunt-end/MspI fragment was ligated, using T4 ligase, together with the large HindIII/blunt end fragment, obtained from pMH43-101 as previously described, and with a MspI/HindIII fragment obtained from a MspI and HindIII digestion of the vector M13-w/43K-#3TGA->TGG. This resulted in the intermediate pMH43-103.

The plasmid pMH43-103 was digested with SspI and BamHI, to form a BamHI/SspI fragment containing araB and a portion of the 5' end of the 43KDa gene. pMH43-101 was digested with HindIII and BamHI, yielding a large HindIII/BamHI fragment containing the majority of the plasmid. The BamHI/SspI and HindIII/BamHI fragments were then joined together, using T4 ligase, with a SspI/HindIII fragment obtained from the vector M13-w/43K-#4TGA->TGG by SspI and HindIII digestion. The resulting intermediate was pMH43-104. DNA sequencing showed a 6 bp deletion at the junction of the blunt-ended NcoI and SstI sites. No expression of the 43 kd regressen protein by this plasmid was found in *E. coli* strain MC1061 when induced with L-arabinose.

The plasmid pMH43-104 was digested with HindIII and MspI. pMH43-105 was digested with MspI and BamHI. The resulting HindIII/MspI and MspI/BamHI fragments were ligated together with the large HindIII/BamHI fragment previously described (from pMH43-101), using T4 ligase, to form a product, pMH43-106, which expressed an intracellular 43 kd regressen protein when transformed into *E. coli* strain MC1061 and induced with L-arabinose. Plasmid pMH43-106 was deposited in *E. coli* MC1061 on Sep. 15, 1988 under accession number TCC 67798 with the American Type Culture Collection, 2301 Parklawn Drive, Rockville, Md. 20852. Example 15 discloses the use of pMH43-106 to express the 43 kd protein.

The plasmid pMH43-102 was digested with HindIII and EcoRI, yielding a HindIII/EcoRI fragment containing the 3' end of the 43 kd gene. This fragment was inserted, using T4 ligase, into the pMH43-106 plasmid which had been cut with EcoRI and HindIII. The resulting product, pMH43-108, was also used to express the intracellular 43 kd regressen protein in *E. coli* strain MC1061. Plasmid pMH43-108 was deposited in *E. coli* MC1061 on Sep. 15, 1988 under accession number ATCC 67800 with the American Type Culture Collection, 12301 Parklawn Drive, Rockville, Md. 20852. Plasmid pMH43-108 has a 300 bp segment removed from outside of the 3'-end of the 43 kd gene, compared to plasmid pMH43-106. The *E. coli* strain MC1061 containing pMH43-108 expresses the 43 kd regressen protein at a higher level than the MC1061 cells containing pMH43-106.

EXAMPLE 14

Expression of Recombinant RAAs

A gene encoding a 55 kd araB-38 kd fusion proten which is under regulation of the *Salmonella typhimurium* araB promoter was expressed in *E. coli* strain MC1061 (Casadaban et al., *J. Mol. Biol.*, 138, 179–207 (1980). The plasmid containing cells were grown in TYE medium (15 g tryptone, 10 g yeast extract, 5 g NaCl/liter) to O.D. 0.4 and L-arabinose was added to a final concentration of 0.4% to induce the araB promoter. The culture was allowed to grow overnight before harvest. The fusion protein which was localized Plasmid pMH43-108 has a 300 bp segment removed from in inclusion bodies inside the cells was detected by SDS-PAGE analysis of inclusion bodies followed by Western immunoblot analysis using rabbit antiserum against *M. hyorhinis* 38 kd antigen.

The mature 38 kd antigen gene (without the signal sequence), which is directly under regulation of the *S. typhimurium* araB promoter on plasmid pMH38-110, was expressed in *E. coli* strain MC1061 as described above. The 38 kd antigen was produced inside of *E. coli* cells as a soluble protein and its identity was confirmed by Western blotting as described above.

The 38 kd antigen gene with its native signal sequence, which is under regulation of the *S. typhimurium* araB promoter on plasmid pMH38-113, was expressed in *E. coli* strain MC1061 as described above. The 38 kd antigen produced was localized intracellularly in the soluble fraction as well as in the medium as judged by Western blotting described above.

The mature 43 kd antigen gene, which is under regulation of the *S. typhimurium* araB promoter on plasmid pMH43-106, was expressed in *E. coli* strain MC1061 as described previously. The *E. coli* produced 43 kd antigen which was localized in the soluble fraction inside the cells, and its identity was confirmed by Western blotting following SDS-PAGE using rabbit antiserum against *M. hyorhinis* 43 kd antigen.

EXAMPLE 15

Fermentation of *E. coli* Strain MC1061 Containing pMH38-110 or pMH43-106

One milliliter of culture thawed from liquid nitrogen storage was inoculated into 100 ml TYE broth containing 100 μg/ml of ampicillin (TYE+Amp). The culture was incubated at 32° C. and 250 rpm until the cell density reached 200 Klett units (red filter). The culture was then diluted 1 to 10 into 900 ml of TYE +Amp in a 4-liter shake flask and allowed to grow for 3 h at 32° C. and 250 rpm prior to inoculation into a 14-liter fermentor.

The initial batch medium used for fermentation was as follows; pancreatic digest of casein, 8 g/l; yeast extract, 8 g/l; $KH_2PO_4$, 3 gl; $Na_2HPO_4$, 6 g/l; NaCl, 0.5 g/l; $NH_4Cl$, 4 g/l; glycerol, 16 g/l; $CaCl_2 (2H_2O)$, 0.022 g/l; $MgSO_4 (7H_2O)$, 0.25 g/l; thiamine HCl, 0.01 g/l. The feeding solution contains: pancreatic digest of casein, 83 g/l; yeast extract, 83 g/l; glycerol, 83 g/l; $CaCl_2 (2H_2O)$, 0.12 g/l; $MgSO_4 (2H_2O)$, 1.4 g/l; thiamine HCl, 0.01 g/l.

Approximately 1 liter of seed culture was inoculated into 9 liter of initial medium. The growth conditions were: pH 7.0; temperature, 32° C.; agitation, 800 rpm; aeration, 1 uvm. At a cell density of 10 $OD_{600}$, 50 g of arabinose was added to the culture to induce expression of the product. The temperature was immediately shifted to 37° C. to optimize the induction.

Dissolved oxygen level was maintained at 20% saturation by increasing the agitation, and later aeration, as the growth continued. A sudden spike on % saturation occurring between 20 and 30 $OD_{600}$ called for the need to commence the feeding process. A continuous gradient feed system was used to control the dissolved oxygen level at 20%.

Fermentation is terminated at 12-14 hr after induction. Cells were harvested by a Westfalia centrifuge model SA-1 (Centrico, Northvale, N.J.). The cells were then pelleted by spinning at 8,000 rpm using a Beckman JA-10 rotor (Fullerton, Calif.) for 30 minutes.

EXAMPLE 16

Purification of *E. coli*-expressed 38 kd Antigen

MC1061 (pMH38-110) cells as described above were ruptured in a French press or in a Gaulin mill in 20 mM phosphate buffer pH 7.4 containing 150 mM NaCl. The disruptate was spun at 10,000 rpm for 20 min in a JA-20 rotor (Beckman Instruments, Fullerton, Calif.) The supernatant from the centrifugation of the disruptate was spun at 40,000 rpm for 1 hr in a Ti 60 rotor in a Beckman ultracentrifuge. The resulting supernatant was dialyzed against 20 mM phosphate buffer, pH 7.8.

The dialyzate was loaded on a DEAE cellulose column (which includes quaternary ammonium groups bonded to cellulose) equilibrated with 20 mM phosphate buffer, pH 7.8. The 38 kd antigen does not bind to this column; and flow-through fractions containing the antigen were pooled The pH of the pooled fractions was adjusted to 4.8 with acetic acid, and the pooled fractions were loaded onto an SP-Sephadex ® column equilibrated with 20 mM Na-acetate pH 4.8. The 38 kd antigen binds to SP-Sephadex ® (which includes sulfopropyl groups bonded to a dextran compound) but was eluted with a 0-300 mM NaCl gradient. Fractions containing the 38 kd antigen were identified by SDS-PAGE analysis. Fractions containing 38kDa antigen were pooled, diluted four-fold with 20 mM Na-acetate at pH 4.8, and loaded onto a heparin-agarose column equilibrated with 20 mM Na-acetate at pH 4.8. The 38 kd antigen bound to the heparin-agarose and was eluted with a 0-300 mM NaCl gradient. Fractions containing 38 kd antigen were identified by SDS-PAGE analysis. The fractions containing purified 38 kd antigen were stored frozen at −20° C.

EXAMPLE 17

Purification of *E. coli*-expressed 43 kd Antigen

MC1061 cells prepared as described above were ruptured by French press or Gaulin mill in a 20 mM phosphate buffer at pH 7.4 containing 150 mM NaCl. The disruptate was spun at 10,000 rpm for 20 min in a JA-20 rotor. The supernatant from the centrifugation of the disruptate was spun at 40,000 rpm for 1 hr in a Ti 60 rotor in a Beckmann ultracentrifuge. The resulting supernatant was dialyzed against 20 mM phosphate buffer, pH 7.4.

The dialyzate was loaded on a DEAE cellulose column equilibrated with 20 mM phosphate buffer, pH 7.4. The 43 kd antigen does not bind to a this column; and flow-through fractions containing the antigen were pooled. The pH of the pooled fractions was adjusted to 4.8 with acetic acid, and the pooled fractions were loaded onto a heparin-agarose column equilibrated with 20 mM Na-acetate at pH 4.8. The 43 kd antigen bound to the heparin-agarose and was eluted with a 0-300 mM NaCl gradient. Fractions were collected and analyzed by SDS-PAGE. Fractions containing the purified 43 kd antigen were pooled and stored frozen at −20° C.

EXAMPLE 18

Development of Rabbit Polyclonal Antibodies to *E. coli*-Expressed 38 kd and 43 kd Antigens Two groups of three rabbits were immunized thrice with 10-50 μg of 38 kd or 43 kd antigen, after mixing with Freund's complete adjuvant with ten days between injections. The rabbits were bled 5-7 days following the third injection. The development of antibodies to appropriate antigens was monitored by Western Immunoblot analysis. Both of the above groups developed antibodies to the appropriate antigen (either 38 kd or 43 kd) which reacted with the isolated *E. coli*-expressed 38 kd or 43 kd antigens, respectively. Sera from regressing patients also cross-reacted with *E. coli*-expressed 38 kd and 43 kd antigens.

EXAMPLE 19

Hybridomas Secreting Monoclonal Antibodies to Recombinant RAAS

Hybridomas secreting monoclonal antibodies to recombinant RAAs may be obtained by following the procedure of Example 5 but employing as the antigen a recombinant RAA according to the present invention, for example, a purified 38 kd or a purified 43 kd RAA as disclosed in Example 16 or 17, respectively. Monoclonal antibodies to recombinant RAAs may be isolated from the media in which such hybridomas have been cultured by passing the media over RAAs or over Staphylococcus protein A bound to a column, followed by elution of the purified antibody.

Although the present invention is described in terms of a preferred embodiment, it is understood that modifications and improvements will occur to those skilled in the art. For example, conventional immunological techniques such radioimmunoassay, immunoprecipitation and ELISA may be suitable for detection of regression-associated antigens.

It is contemplated that RAAbs and monovalent variants thereof may be produced by recombinant techniques. RAAbs and fragments thereof may also be employed in passive immunization procedures. [Beutler et al., *Science*, 229, 869-871 (1985)]. Anti-idiotypic antibodies may be raised against RAAbs [Eichmann et al., *CRC Crit. Rev. Immunol.*, 7, 193-227 (1987)] and employed in immunotherapy and purification of RAAbs as described for RAAs above. In particular, RAAbs may be employed in passive immunization therapies as understood by those skilled in the art.

Accordingly, it is intended that the appended claims include all such equivalent variations which come within the scope of the invention as claimed.

We claim:

1. An isolated nucleic acid consisting of a portion of the *M. hyorhinis* genome which encodes a regression-associated antigen, wherein said nucleic acid consists essentially of a nucleotide sequence selected from the group consisting of:
   the nucleotide sequence as shown in FIG. 1;
   a nucleotide sequence which encodes the same sequence of amino acids as encoded by the nucleotide sequence shown in FIG. 1.

2. A vector comprising a nucleotide sequence as recited in claim 1.

3. The vector as recited in claim 2 wherein said vector is pMH38-110 which is deposited in ATCC 67799.

4. The vector as recited in claim 2 wherein said vector is pMH38-1113 which is deposited in ATCC 67801.

5. A host cell comprising the vector as recited in claim 4.

6. The host cell as recited in claim 5 wherein said host cell is an *E. coli* cell.

7. The host cell as recited in claim 5 wherein said host cell is deposited in ATCC 67799.

8. The host cell as recited in claim 5 wherein said host cell is deposited in ATCC 67801.

* * * * *